United States Patent
Coquerel et al.

(10) Patent No.: US 8,546,344 B2
(45) Date of Patent: Oct. 1, 2013

(54) CRYSTALLINE PHASES OF 5,6-DICHLORO-2-(ISOPROPYLAMINO)-1-β-L-RIBOFURANOSYL)-1H-BENZIMIDAZOLE

(75) Inventors: Gerard Coquerel, Boos (FR); Guillaume Levilain, Deville les Rouen (FR); Marie-Noelle Petit, Mount Saint Aignan (FR); Servane Coste-Leconte, Saint Romy les Chevreuse (FR)

(73) Assignee: ViroPharma Incorporated, Exton, PA (US)

( * ) Notice: Subject to any disclaimer, the term of this patent is extended or adjusted under 35 U.S.C. 154(b) by 13 days.

(21) Appl. No.: 13/282,510

(22) Filed: Oct. 27, 2011

(65) Prior Publication Data

US 2012/0178709 A1    Jul. 12, 2012

Related U.S. Application Data

(60) Provisional application No. 61/407,622, filed on Oct. 28, 2010.

(51) Int. Cl.
*C07H 19/052* (2006.01)
*A61K 31/7028* (2006.01)
*A61P 31/22* (2006.01)

(52) U.S. Cl.
USPC .......................................... 514/43; 536/28.9

(58) Field of Classification Search
None
See application file for complete search history.

(56) References Cited

U.S. PATENT DOCUMENTS

| 6,077,832 A | 6/2000 | Chamberlain et al. |
| 6,469,160 B1 | 10/2002 | Glover et al. |
| 6,482,939 B1 | 11/2002 | Hodgson et al. |

OTHER PUBLICATIONS

Flack, H.D., "On Enantiomorph-Polarity Estimation", Acta. Cryst., A39: 876-881 (1983).

*Primary Examiner* — Layla Bland
*Assistant Examiner* — Bahar Craigo
(74) *Attorney, Agent, or Firm* — Patrick J. Hagan; Dann, Dorfman, Herrell and Skillman, P.C.

(57) ABSTRACT

The invention relates to novel crystalline phases of 5,6-dichloro-2-(isopropylamino)-1-(β-L-ribofuranosyl)-1H-benzimidazole (Maribavir), pharmaceutical compositions thereof and their use in medical therapy.

10 Claims, 16 Drawing Sheets

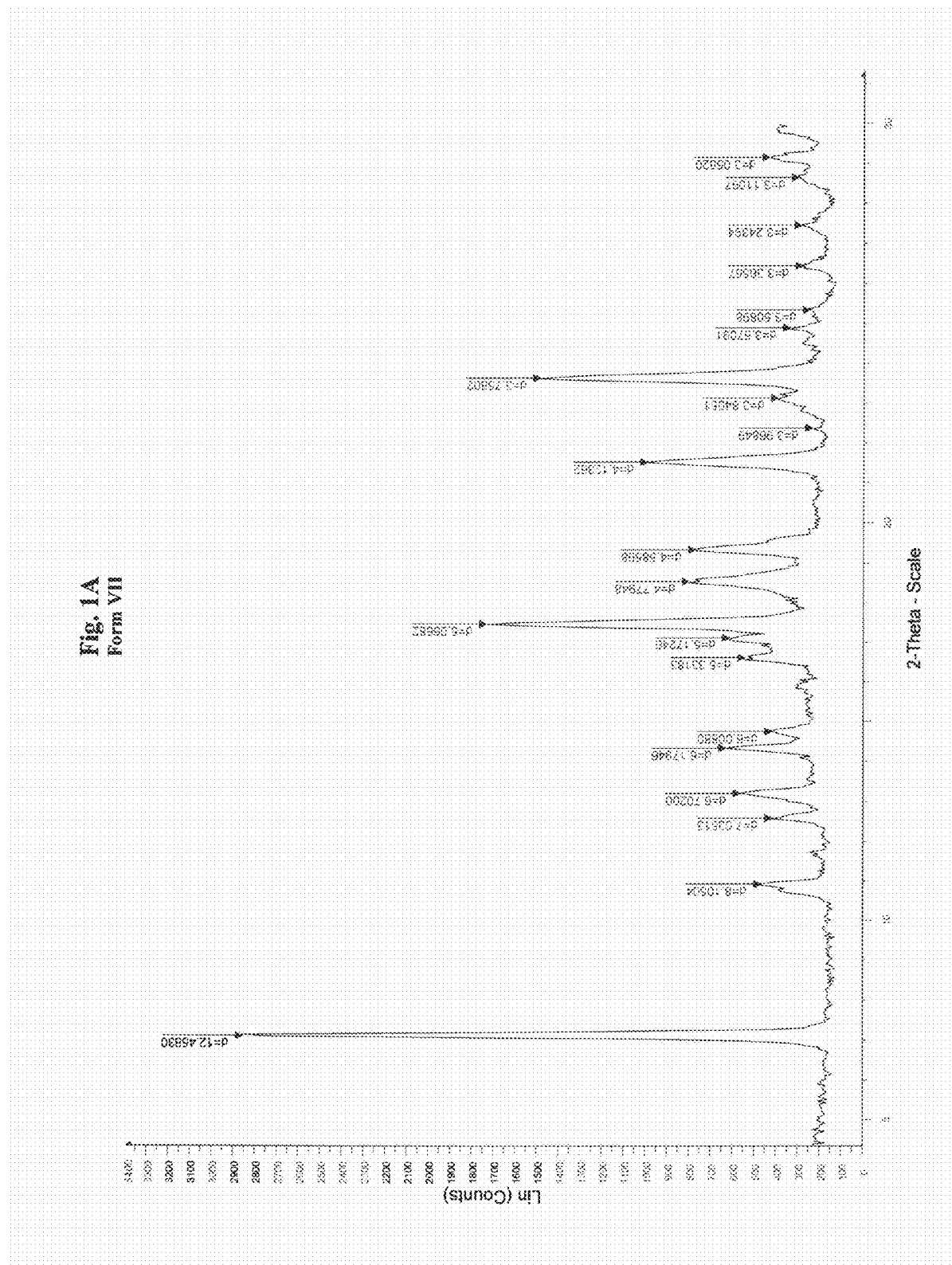

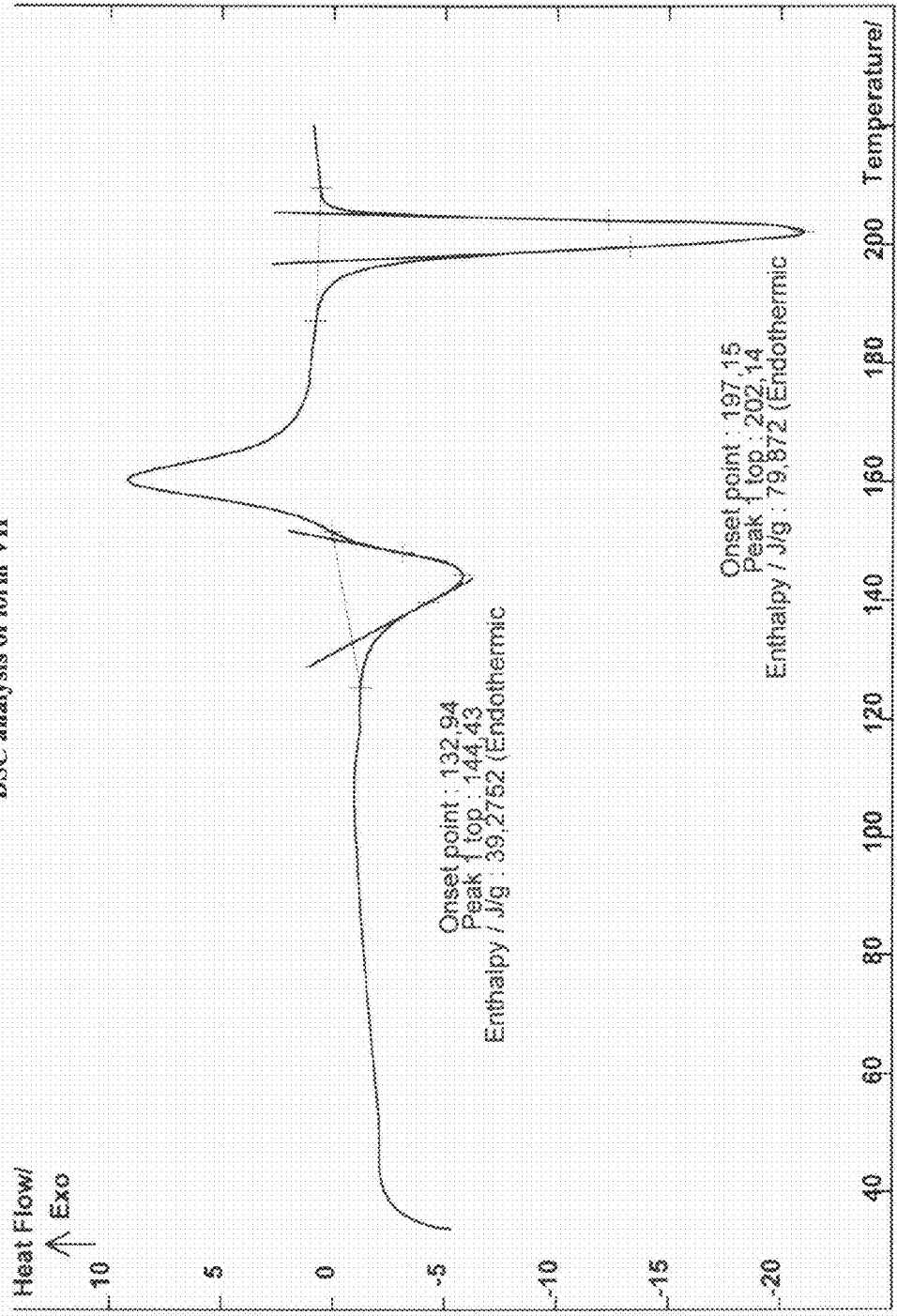

IR spectrum of form VII

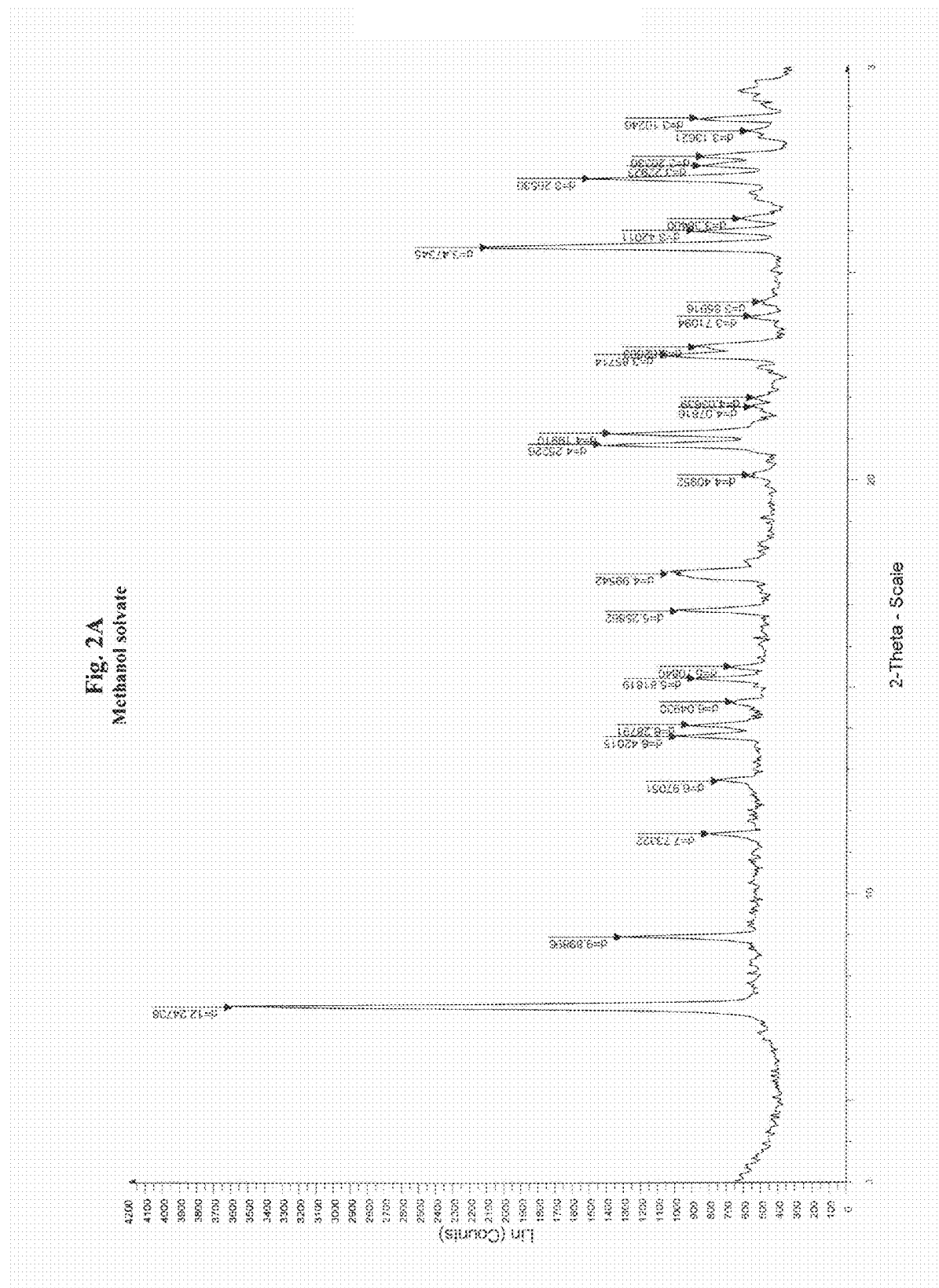

Methanol solvate as a function of temperature

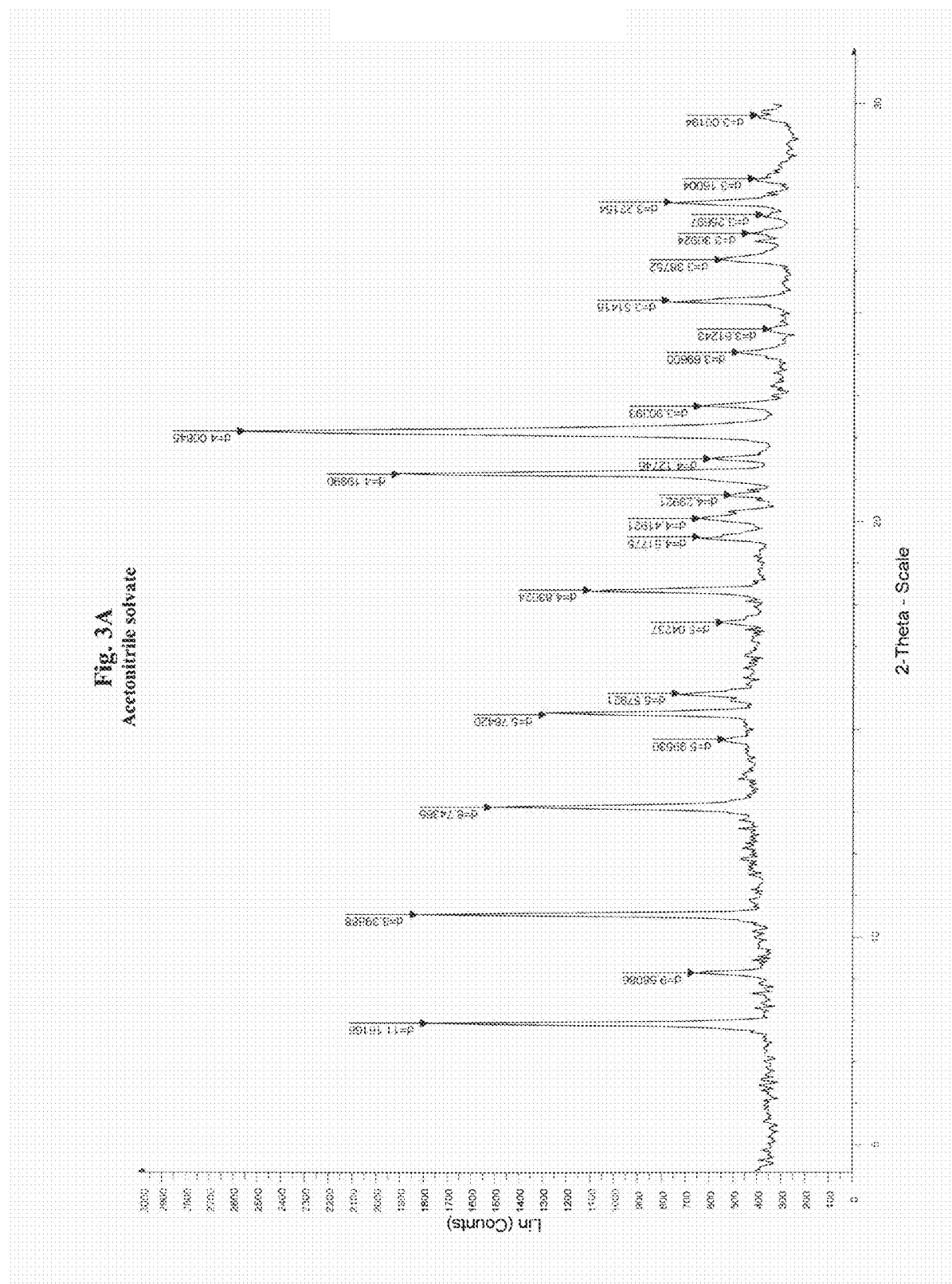

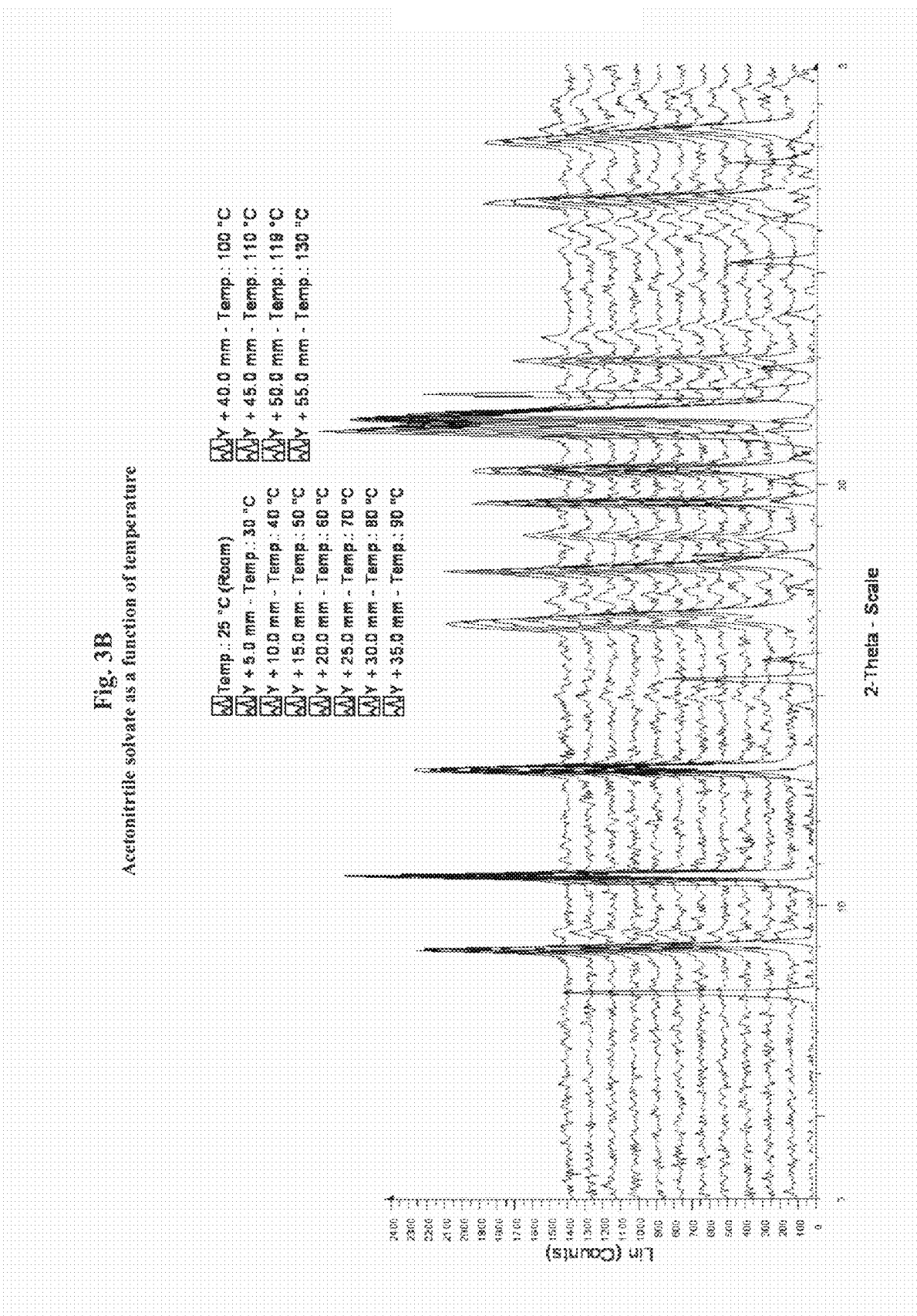

Ethyl acetate solvate

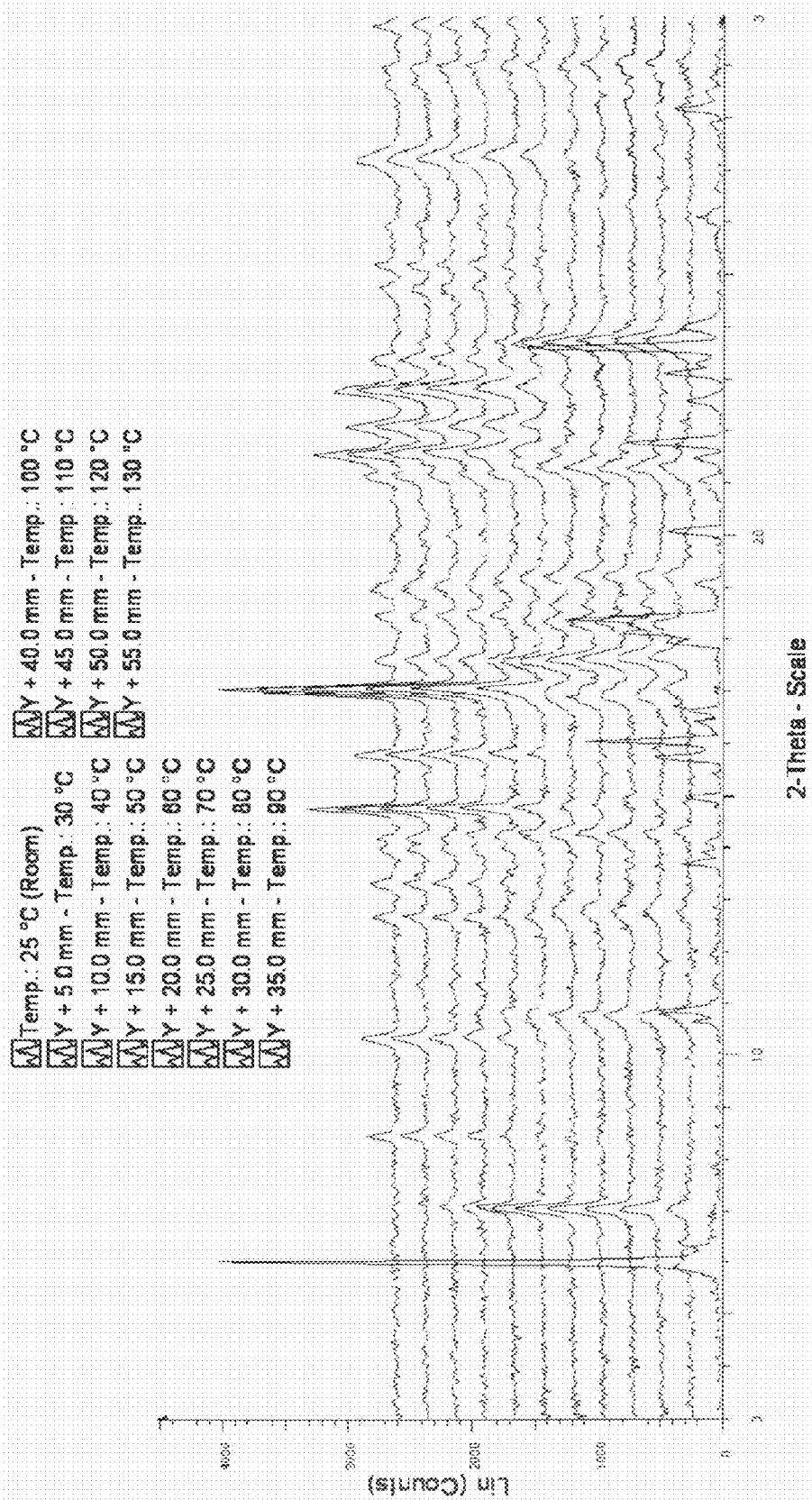

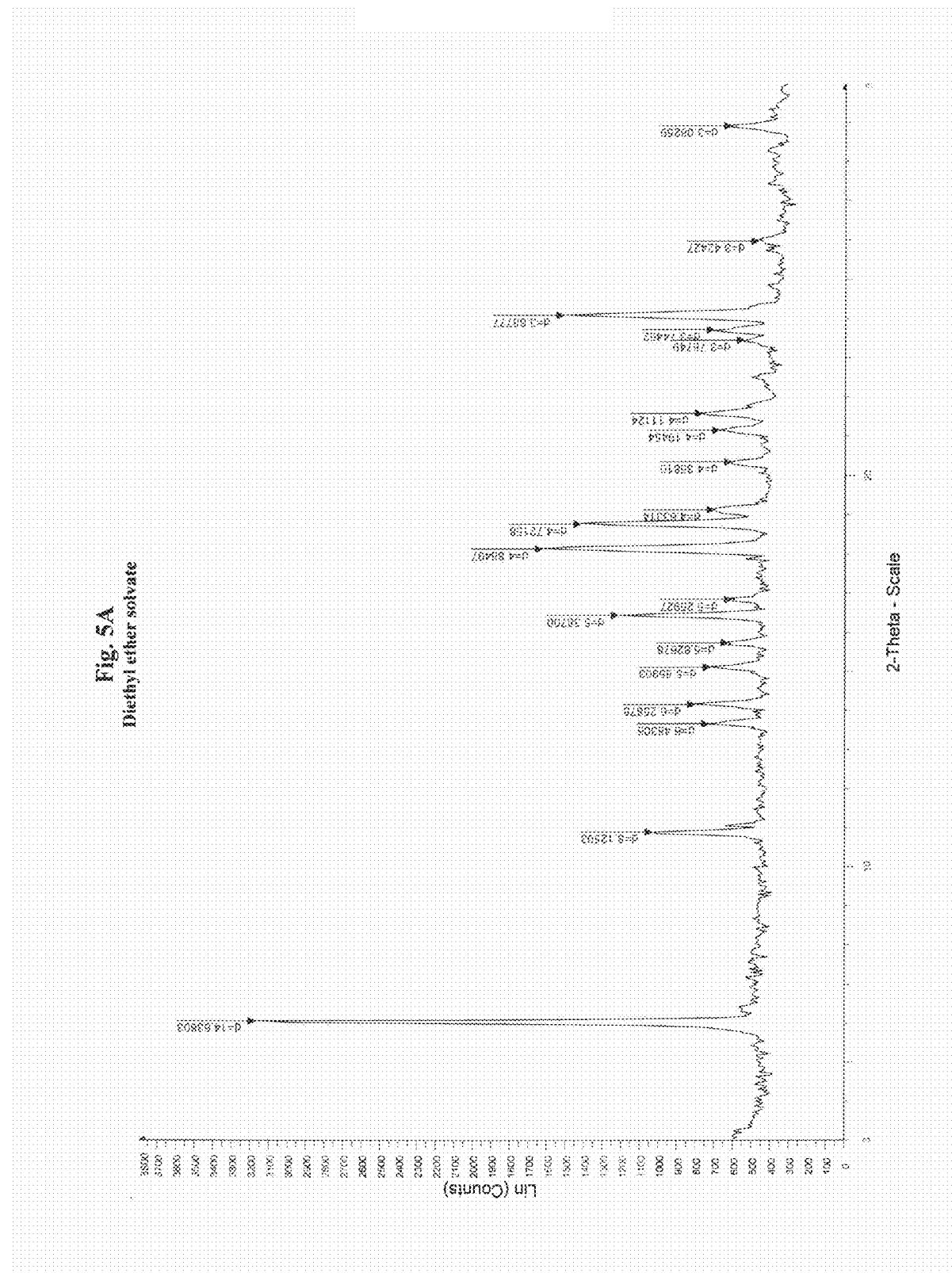

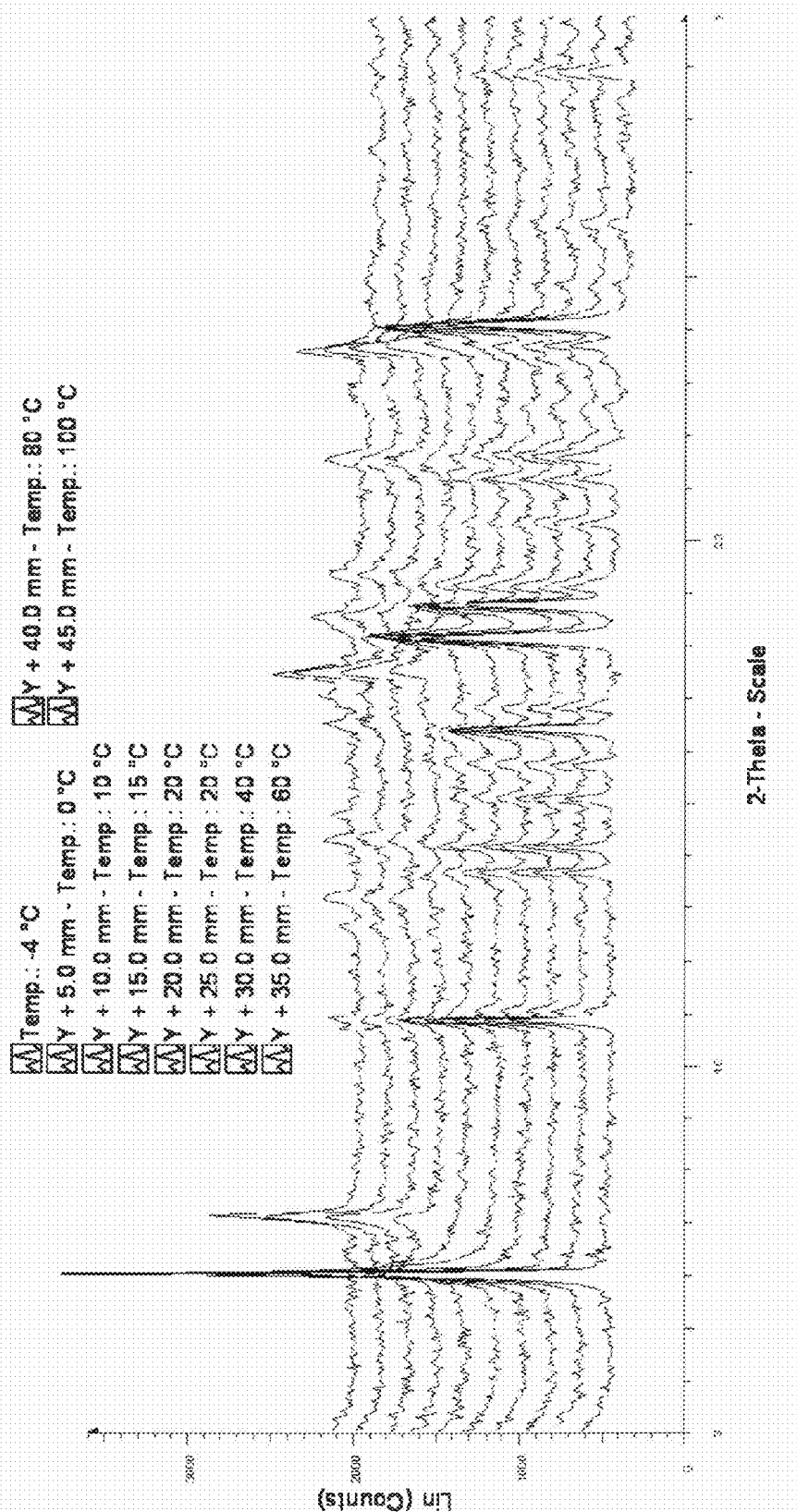

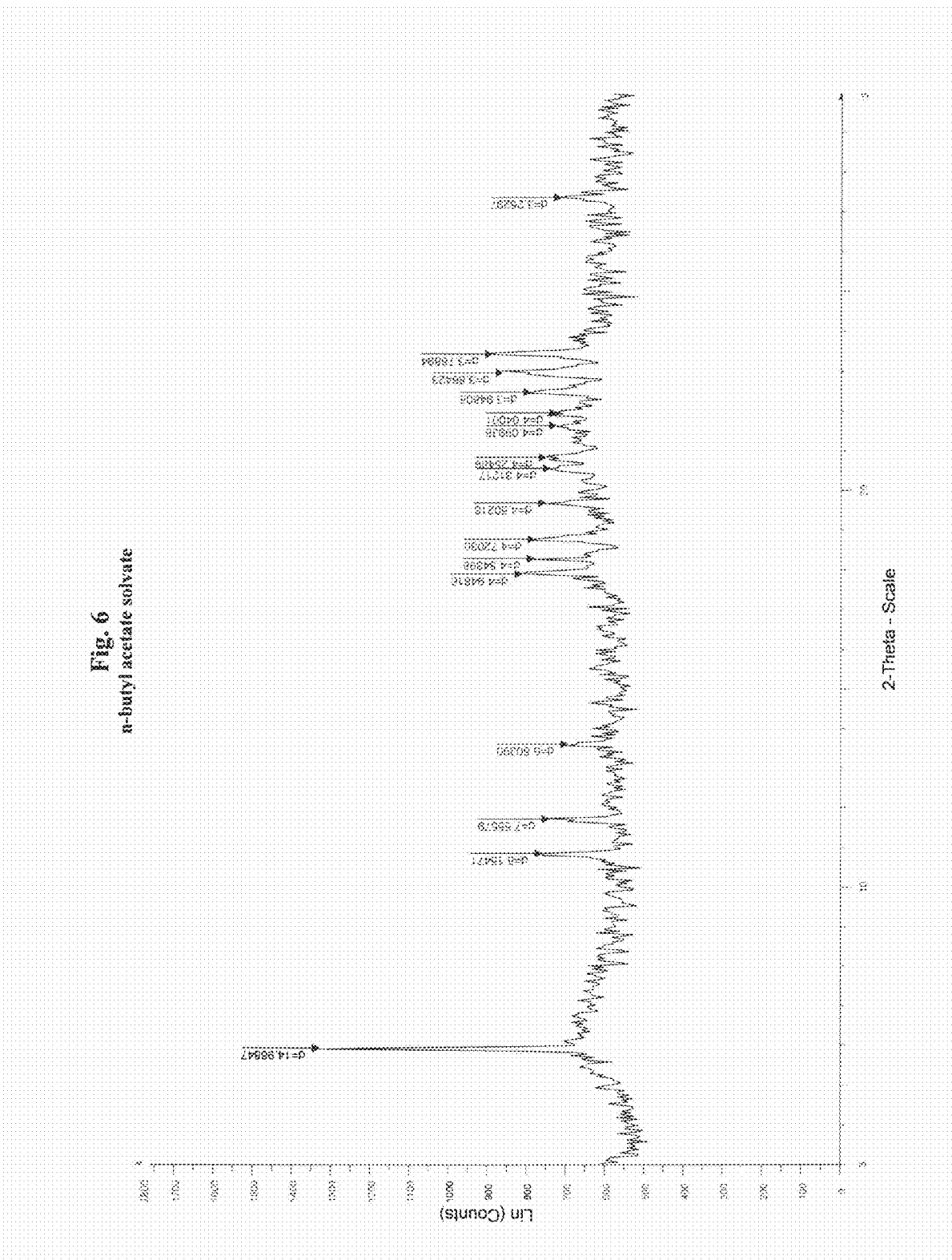

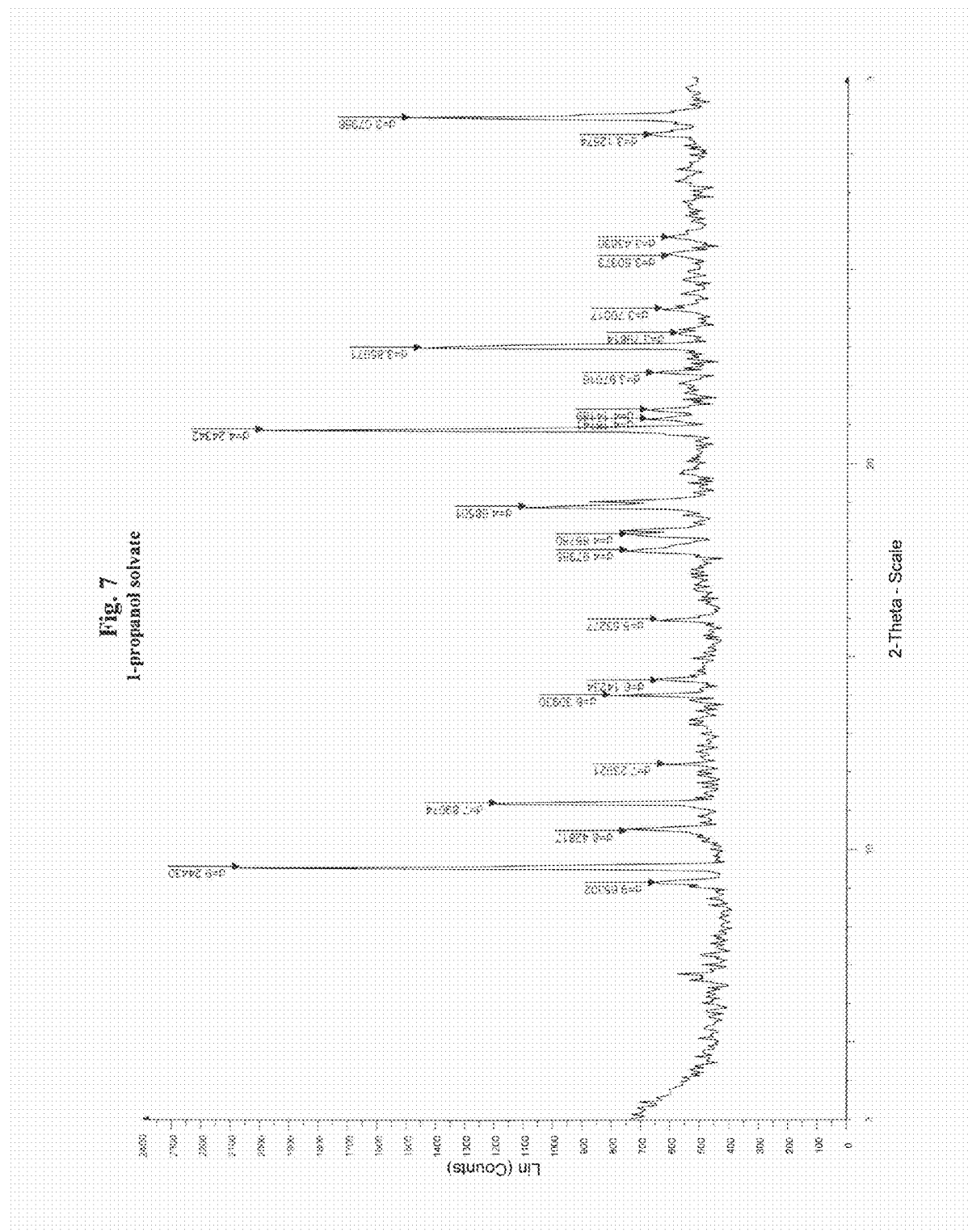

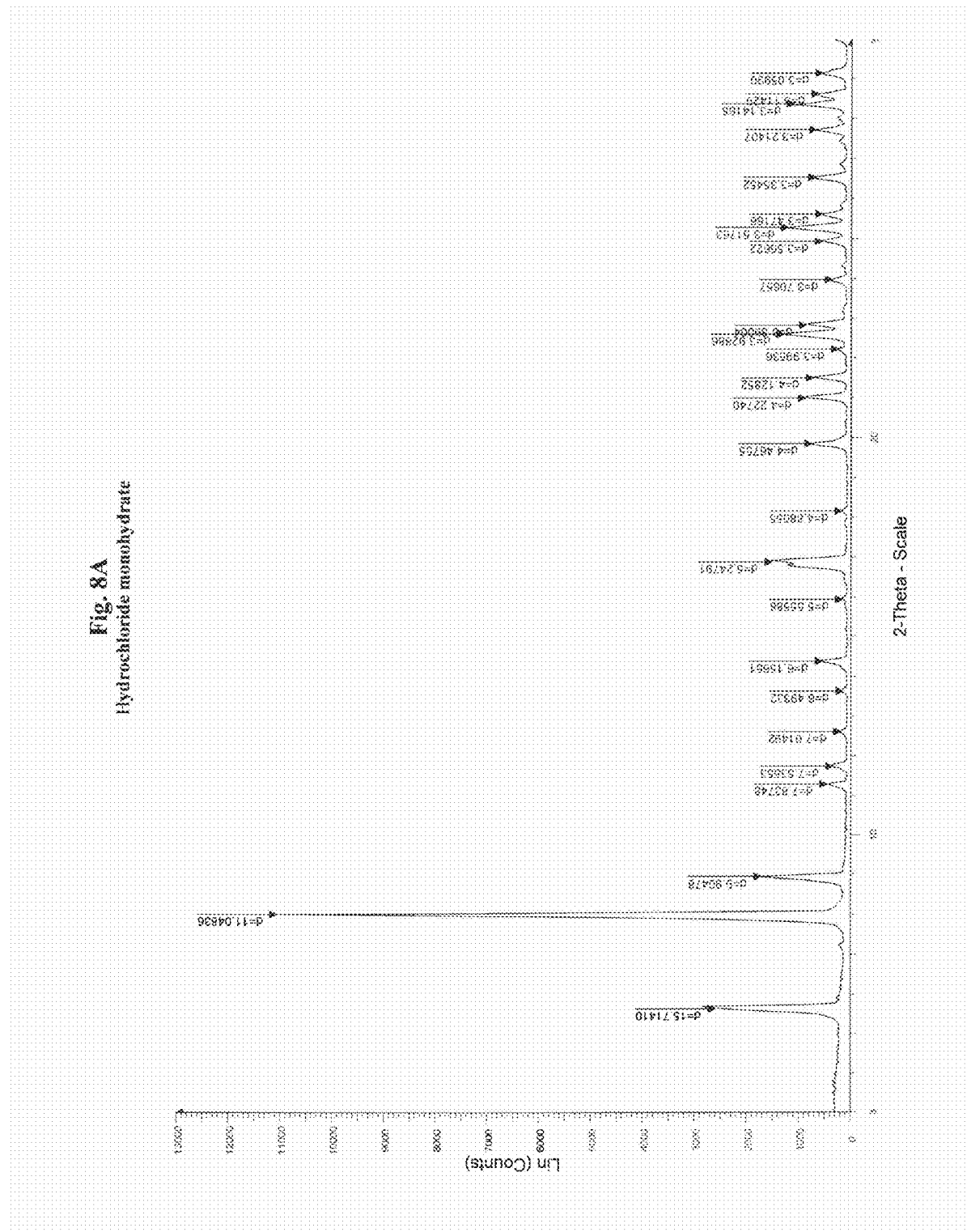

TGA-DSC on the hydrochloride monohydrate

CRYSTALLINE PHASES OF 5,6-DICHLORO-2-(ISOPROPYLAMINO)-1-β-L-RIBOFURANOSYL)-1H-BENZIMIDAZOLE

CROSS-REFERENCE TO RELATED APPLICATIONS

The present application claims the benefit of U.S. Provisional Patent Application No. 61/407,622, filed Oct. 28, 2010, the entire disclosure of which is incorporated by reference herein.

BACKGROUND OF THE INVENTION

The present invention relates to an unsolvated crystalline form, various solvates, and the HCl monohydrate salt of the antiviral compound 5,6-dichloro-2-(isopropylamino)-1-(β-L-ribofuranosyl)-1H-benzimidazole (also known as 1263W94; maribavir; a compound of formula (I) below), pharmaceutical formulations comprising such crystalline form, solvates and the HCl monohydrate, and their use in therapy.

5,6-dichloro-2-(isopropylamino)-1-(β-L-ribofuranosyl)-1H-benzimidazole (1263W94; maribavir) is a benzimidazole derivative useful in medical therapy. U.S. Pat. No. 6,077,832 discloses 5,6-dichloro-2-(isopropylamino)-1-(β-L-ribofuranosyl)-1H-benzimidazole and its use for the treatment or prophylaxis of viral infections such as those caused by herpes viruses. The compound as disclosed in U.S. Pat. No. 6,077,832 is an amorphous, non-crystalline material.

The structure of 5,6-dichloro-2-(isopropylamino)-1-(β-L-ribofuranosyl)-1H-benzimidazole, a compound of formula (I) is shown below:

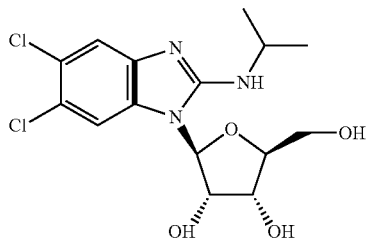 [SMILES: CC(C)Nc1nc2cc(Cl)c(Cl)cc2n1[C@H]1O[C@@H](CO)[C@H](O)[C@@H]1O]

The preparation of certain crystalline forms and solvate forms of 5,6-dichloro-2-(isopropylamino)-1-(β-L-ribofuranosyl)-1H-benzimidazole, as well as pharmaceutical formulations thereof and their use in therapy are described in U.S. Pat. Nos. 6,469,160 and 6,482,939.

Different polymorphs normally have different solubilities, different residence times in the body and different therapeutic values. In view of these differences, it is important in drug development to determine the properties, and control, to the extent possible, the presence of polymorphs in any drug product administered in crystalline form that is submitted for regulatory approval.

SUMMARY OF THE INVENTION

It has now been discovered, in accordance with this invention, that 5,6-dichloro-2-(isopropylamino)-1-(β-L-ribofuranosyl)-1H-benzimidazole (1263W94; maribavir) may be prepared in a novel unsolvated crystalline form, solvate forms and as the HCl monohydrate salt in addition to those previously described.

According to one aspect of the invention there is provided the compound of formula (I) in a novel crystalline form, Form VII. Form VII is defined by the X-ray powder diffraction pattern (XRPD) illustrated in FIG. 1, the DSC profile illustrated in FIG. 2 and the IR spectrum in FIG. 3, which is obtained in the manner described in the examples that follow.

In another aspect of the invention various solvates of the compound of formula (I) and the hydrochloride are provided, which are selected from the group of methanol, acetonitrile, ethyl acetate, diethylether, n-butylacetate, 1-propanol solvates, hydrochloride monohydrate or mixtures thereof. These phases, which are defined by their respective X-ray powder diffraction patterns, illustrated in FIGS. 2 to 8, are obtained using the procedures exemplified below.

In still with another aspect of the present invention, pharmaceutical compositions are provided comprising one or more of the polymorphs described herein and one or more pharmaceutically acceptable carriers and/or excipients. Suitable carriers and excipients for the formulation of pharmaceutically acceptable compositions comprising the polymorphs of this invention are well known in the art and are disclosed, for example, in U.S. Pat. No. 6,077,832.

The present invention also provides a method for the treatment or prophylaxis of a viral infection, particularly a herpes infection, such as cytomegalovirus (CMV) infection, as well as disease caused by hepatitis B and hepatitis C viruses in a patient, e.g. a mammal such as a human, which comprises administering to the patient an effective antiviral amount of the compound of formula (I) as unsolvated crystalline Form VII or a novel solvate of such compound or the HCl monohydrate salt.

The present invention also provides the use of the compound of formula (I) anhydrous crystalline forms and solvates in the preparation of a medicament for the treatment or prophylaxis of a viral infection.

In a further aspect of the invention, there is provided the compound of formula (I) as a mixture of any two or more of the unsolvated crystalline form, VII, and/or solvates, and/or the HCl monohydrate salt described herein, or as a mixture with amorphous material or with one or more of the anhydrate crystalline forms and/or solvates previously described.

The novel crystalline form. solvates, and the HCl monohydrate salt of the present invention are new crystalline phases of the compound 5,6-dichloro-2-(isopropylamino)-1-(β-L-ribofuranosyl)-1H-benzimidazole that have different chemical and/or physical properties relative known crystalline phases of the compound. For example, Form VII has a relatively low melting point. The ethyl acetate solvate can be isolated directly from the mother ethyl acetate liquor and can be used as an intermediate in the preparation of purified Form VI via a desolvation process. Depending on the desolvation conditions, the Form VII may (may not) be formed as an intermediate during preparation of Form VI from the ethyl acetate solvate. Purified Form VI may also be prepared by similar processes of desolvation with the corresponding diethyl ether solvate. The novel crystalline form and solvates described herein, which are characterized by their X-ray powder diffraction patterns, thermogravimetric analysis (TGA) and differential scanning calorimetry (DSC) profiles and IR spectra, can be produced in various conventional solid and liquid suspension dose forms for therapeutic use in the manner previously described in U.S. Pat. Nos. 6,469,160 and 6,482,939.

BRIEF DESCRIPTION OF THE DRAWINGS

FIG. 1A sets forth identifying data for Form VII of the compound of Formula I, above, including X-ray powder diffraction pattern;

FIG. 1B sets forth identifying data for Form VII of the compound of Formula I, above, including DSC profile;

FIG. 3 sets forth identifying data for acetonitrile solvate of the compound of Formula I, above, including 3A, X-ray powder diffraction pattern at 20° C. and 3B, temperature resolved X-ray powder diffraction patterns, the X-ray powder diffraction pattern being obtained using a diffractometer equipped with a Ni Filter in order to remove most part of the CuKβ radiation;

FIG. 5 sets forth identifying data for diethyl ether solvate of the compound of Formula I, above, including, 5A X-ray powder diffraction pattern at 20° C.; and 5B, temperature resolved X-ray powder diffraction patterns, the X-ray powder diffraction pattern being obtained using a diffractometer equipped with a Ni Filter in order to remove most part of the CuKβ radiation;

FIG. 6 sets forth identifying data for n-butyl acetate solvate of the compound of Formula I, above, including X-ray powder diffraction pattern at 20° C., the X-ray powder diffraction pattern being obtained using a diffractometer equipped with a Ni Filter in order to remove most part of the CuKβ radiation;

FIG. 7 sets forth identifying data for 1-propanol solvate of the compound of Formula I, above, including X-ray powder diffraction pattern at 20° C., the X-ray powder diffraction pattern being obtained using a diffractometer equipped with a Ni Filter in order to remove most part of the CuKβ radiation;

DETAILED DESCRIPTION OF THE INVENTION

Figure 1C:
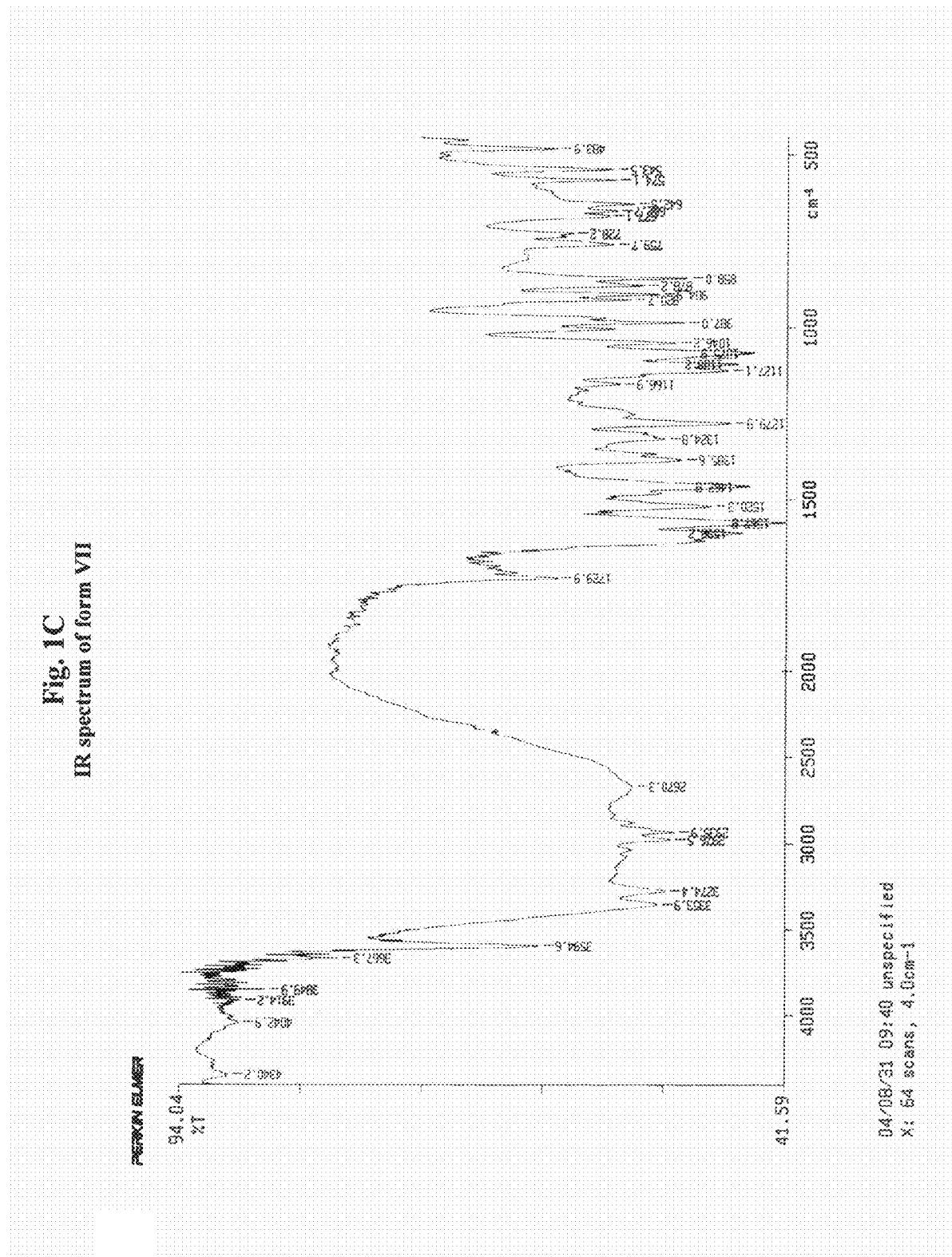
FIG. 1C sets forth identifying data for Form VII of the compound of Formula I, above, including IR spectrum.

"Polymorph", as generally understood, refers to a solid phase of a compound which occurs in several distinct forms due to different arrangements and/or confirmations of its molecular crystal lattice. As used herein, the term "polymorph" includes solid phases resulting from packing polymorphism and conformational polymorphism, and therefore may include different unsolvated crystal forms of a compound, and may include the crystalline forms made by removing the solvent from a solvate.

In particular embodiments of the present invention, pure, single polymorphs as well as mixtures comprising two or more different polymorphs are contemplated. A pure, single polymorph may be substantially free from other polymorphs. "Substantially free", as used herein, signifies that other polymorph(s) are present in an amount less than about 10 weight percent, more preferably less than about 1 weight percent and most preferably less than about 0.5 weight percent.

Additional technical terms used to describe the present invention, and their meanings, are provided below.

Crystalline phase (material): is a solid substance in which the atoms, molecules or ions are arranged in an orderly repeated pattern extending in all three spatial dimensions (called crystal lattice) that give diffraction peaks when exposed to X-rays.

Amorphous phase (material): is a solid or semi-solid substance that unlike the crystalline phase has no long range order of molecular packing or well-defined molecular conformation if the molecules are conformationally flexible.

Form: is a crystalline phase of a substance without solvent or water of crystallization contained in the crystal lattice that possesses distinct arrangements and/or conformations of the molecules in the crystal lattice detectable by X-ray powder diffraction pattern (XRPD) and single crystal X-ray crystallography among other techniques (that is, spectroscopic techniques).

Forms with cavities: forms that contain cavities, channels or void spaces (all of which are referred to here as cavities) in the crystal lattice. These forms may contain solvents and/or water in stoichiometric or non-stoichiometric amounts in the cavities.

Anhydrate (polymorph): a form with no water of crystallization in the crystal lattice; residual surface water not making up part of the crystal lattice might be present (some residual minor surface water may be present).

Asolvate—Anhydrate (polymorph): a form with no solvent and/or water of crystallization in the crystal lattice; residual surface solvent and/or water not making part of the crystal lattice might be present.

Anhydrous (polymorph): a form with no water of crystallization in the crystal lattice and also no residual surface water.

Asolvate—Anhydrous (polymorph): a form with no solvent and/or water of crystallization in the crystal lattice and also no residual surface solvent and/or water.

Solvate: a crystallized phase that contains molecules of the solvent of crystallization in a stoichiometric and/or non-stoichiometric amount in the crystal lattice. The solvent of crystallization may be water in which case the solvate is aptly referred to as "hydrate." A stoichiometric solvate contains a discrete amount of solvent relative to the compound molecule in the crystal structure. A non-stoichiometric solvate contains in the crystal lattice a non-discrete or continuous change in the solvent stoichiometry relative to the compound molecules.

Hydrate: a solvate in which the solvent of crystallization contained in the crystal lattice is water. Similar to solvates, hydrates can be stoichiometric or non-stoichiometric.

Mixed hydrate/solvate: solvate in which the solvents of crystallization contained in the crystal lattice are both solvent and water. Mixed hydrates/solvates can be stoichiometric and/or non-stoichiometric.

Isomorphic solvates: are solvates that possess similar crystal structure properties (same symmetries and similar unit cell parameters and crystal packing) while having different chemical compositions (i.e., different solvent and/or water molecules incorporated in the crystal lattice). The unit cell parameters of the isomorphic solvates within a class can differ as a function of the size of the incorporated solvent. The solvent molecules of an isomorphic solvate can be hydrogen bonded to the parent molecule and/or contained in the cavities of the crystal structure (also called a void space or channel).

Isomorphous desolvate: crystallized phase that does not contain solvent or water anymore but whose structure is very similar to that of the former solvate or hydrate.

Molecular ratio: the molecular ratio in a solvate of solvent molecules relative to the compound molecules in the crystal structure. Depending on the solvate, the molecular ratio of in the crystal structure may be either a stoichiometric ratio, e.g., a molecular ratio of 1:1, or a non-stoichiometric ratio.

The X-ray powder diffraction pattern of crystalline form VII, the various solvates and the HCl monohydrate salt of the present invention can be determined using conventional techniques and equipment known to those skilled in the art of physical characterization. The diffraction patterns of FIGS. 1A, and 2-8 were obtained with a Siemens D5005 diffractometer system equipped with a Ni Filter in order to remove most part of the CuKβ radiation and a scintillator detector. The powder sample used to generate the X-ray powder diffraction data was prepared by conventional preparation techniques and deposited on the sample holder of the TTK 450 chamber (anton Paar—Austria) This chamber and its regulation hardware were used for temperature resolved XRPD analyses. Zero theta was checked by using Siemens calibrating slits.

A powder sample of Form VII, the various novel solvates, and the HCl monohydrate salt mentioned above was used to produce the X-ray powder diffraction patterns of FIGS. 1A and 2-8, respectively. Form VII and each of the novel solvates exhibit a diffraction pattern with a unique set of diffraction peaks which can be expressed in 2 theta angles (.degree.) or d-spacings (.ANG.) and relative peak intensities.

2 Theta diffraction angles and corresponding d-spacing values account for positions of various peaks in the X-ray powder diffraction pattern. D-spacing values are calculated with observed 2 theta angles and mean copper K.alpha. wavelength using the Bragg equation. Slight variations in observed 2 theta angles and d-spacings are expected based on the specific diffractometer employed and the analyst's sample preparation technique. Greater variation is expected for the relative peak intensities. Identification of the exact crystal form of a compound should be based primarily on observed 2 theta angles or d-spacings with lesser importance placed on relative peak intensities. In a mixture of crystal forms, the strongest diffraction peak for each form may overlap with the diffraction peak of another form. In a mixture of crystal forms, identification may be based on the presence of a lesser intensity peak that does not overlap with the other crystal forms.

Each of the unsolvated crystalline Form VII and/or solvates and/or HCl monohydrate salt of 5,6-dichloro-2-(isopropylamino)-1-(β-L-ribofuranosyl)-1H-benzimidazole can also be identified by the presence of multiple characteristic 2 theta angle peaks including two, three, four, five, six, seven, eight, nine, or ten of the 2 theta angles which are reasonably characteristic of the particular crystalline form.

Some margin of error may be present in each of the 2 theta angle assignments and d-spacings reported herein. The error in determining d-spacings decreases with increasing diffraction scan angle or decreasing d-spacing. The margin of error in the 2 theta angles reported in the following examples for Form VII, the various solvates and the HCl monohydrate salt is approximately ±0.1 degrees for each peak assignment.

Since some margin of error is possible in the assignment of 2 theta angles and d-spacings, the preferred method of comparing X-ray powder diffraction patterns in order to identify a particular crystalline form is to overlay the X-ray powder diffraction pattern of the newly discovered form over the X-ray powder diffraction pattern of a known form. For example, one skilled in the art can overlay on FIG. 1A an X-ray powder diffraction pattern of an unidentified crystalline form of 5,6-dichloro-2-(isopropylamino)-1-(β-L-ribofuranosyl)-1H-benzimidazole, obtained using the methods described herein, and readily determine whether the X-ray diffraction pattern of the unidentified form is substantially the same as the X-ray powder diffraction pattern of Form VII. If the X-ray powder diffraction pattern is substantially the same as FIG. 1A, the previously unknown crystalline form can be readily and accurately identified as Form VII. The same technique can be used to determine if an unidentified crystalline form is any of the solvate forms of 5,6-dichloro-2-(isopropylamino)-1-(β-L-ribofuranosyl)-1H-benzimidazole described herein by overlaying the X-ray powder diffraction pattern over FIGS. 2-8, respectively.

Although 2 theta angles or d-spacings are the primary method of identifying a particular crystalline form, it may be desirable to also compare relative peak intensities. As noted above, relative peak intensities may vary depending upon the specific diffractometer employed, the shape of the crystals (the so-called 'preferential orientation effect'), the crystal size distribution, the quality of the long range order (i.e. the crystallinity) and the analyst's sample preparation technique. The peak intensities are reported as intensities relative to the peak intensity of the strongest peak. The intensity units on the X-ray diffraction plot are counts/sec.

Other methods of physical characterization can also be employed to identify the unsolvated crystalline forms or solvates or the HCl monohydrate salt of the present invention. For example, melting point, differential scanning calorimetry and infrared spectra, are all techniques known to those skilled in the art to be useful for the physical characterization of a crystalline form or solvate. These techniques may be employed alone or in combination to characterize a given anhydrous crystalline form or solvate.

The present invention expressly contemplates mixtures of any of the foregoing unsolvated crystalline form or solvates or the HCl monohydrate salt with one or more of the amorphous compound of formula (I), and/or other anhydrous crystalline forms and solvates previously described. It should be understood that admixtures of a particular crystalline form or solvate with amorphous compound of formula (I) and/or other crystalline forms or solvates may result in the masking or absence of one or more of the foregoing X-ray powder diffraction peaks described above for that particular form. Methods are known in the art for analyzing such admixtures of crystalline forms in order to provide for the accurate identification of the presence or absence of particular crystalline forms in the admixture.

In addition to the foregoing, any of the unsolvated crystalline forms or solvates of the present invention may be in admixture with hydrated crystalline forms. For example in any batch containing the unsolvated crystalline compound of formula (I), there may also be hydrated crystalline forms of the compound or its hydrochloride monohydrate salt form.

The crystalline Form VII, the solvate forms, and the HCl monohydrate salt of the compound of formula (I) described herein are useful as intermediate material(s) for the preparation of active pharmaceutical ingredients (API) and/or drug products that contain the compound of formula (I).

As previously mentioned, crystalline Form VII and the solvate forms of the compound of formula (I) as well as the hydrochloride monohydrate described herein are useful in medical therapy, for example in the treatment or prophylaxis of a viral disease in a patient in need thereof, e.g. a mammal such as a human. The compound of formula (I) unsolvated crystalline Form VII and the solvates of such compound described herein are especially useful for the treatment or prophylaxis of viral diseases such as herpes virus infections, for example, CMV infections, as well as disease caused by hepatitis B and hepatitis C viruses. In addition to its use in human medical therapy, the compound of formula (I) anhydrous crystalline forms and solvates can be administered to other patients for treatment or prophylaxis of viral diseases, for example to other mammals.

As used herein, the term prophylaxis includes the prevention of infection, the prevention of occurrence of symptoms and the prevention of recurrence of symptoms.

Appropriate amounts of the polymorphs described herein for administration in the treatment or prophylaxis of herpes viral infection are essentially the same as described in U.S. Pat. Nos. 6,469,160 and 6,482,939, which also describe suitable dose forms and routes of administration.

The novel crystalline form, solvates, and the HCl monohydrate salt of the invention can be administered conveniently in powder, tablet, capsule or suspension form.

Form VI has been described as the most thermodynamically stable form of 5,6-dichloro-2-(isopropylamino)-1-(β-L-ribofuranosyl)-1H-benzimidazole. The unit cell parameters and space group were stated in U.S. Pat. No. 6,482,939 to be a=b=9.1542 Å, c=41.687 Å with $P4_32_12$ (data recorded at 160 K).

The research leading up to the preparation of the polymorphs described herein involved a careful reexamination of the crystal structure and more especially of the Flack parameter, which led the present inventors to conclude without any doubt that the ribofuranosyl derivative crystallized in the $P4_12_12$ space group, and not in the $P4_32_12$ space group, as previously described. Single crystals suitable for X-ray analysis were obtained by crystallization from ethyl acetate solution at 323 K. The structure was solved in the tetragonal system with the enantiomorphic space group $P4_12_12$. The refinement led to a $R_1$ factor of 0.02 ($F^2>2\sigma(F^2)$) with a Flack parameter of −0.02 (7). When using the $P4_32_12$ space group, a Flack parameter of 1.03 (7) with a similar $R_1$ factor was obtained. The ORTEP view in FIG. 12 presents the asymmetric unit of Form VI having the L configuration. The latter configuration is stabilized by intramolecular hydrogen bonds given in Table 9B. Moreover, several Intermolecular H bonds contribute to the structural cohesion. The main interactions are given in Table 9C. No Cl-Cl distance was found shorter than 4 Å. Representativeness of the single crystal with reference to the raw Form VI was also confirmed. The single crystal X-ray diffraction analysis used to make the space group determination is set forth below in the examples.

The following examples describe the invention in further detail. These examples are provided for illustrative purposes only, and should in no way be considered as limiting the invention.

EXAMPLE 1

Form VII

In a vial, 2.0 g of the 5,6-dichloro-2-(isopropylamino)-1-(β-L-ribofuranosyl)-1H-benzimidazole (crystallized as form VI) were dissolved in 10.0 g of ethyl acetate at room temperature. The solution was completely evaporated under a nitrogen flux during five days. A crystalline powder was obtained. The X-ray powder diffraction pattern of this powder is presented in FIG. 1A. Table 1 below gives the most significant XRPD peaks. The DSC curve is presented in FIG. 1B and the IR spectrum is presented in FIG. 1C.

TABLE 1

| XRPD pattern of form VII | | | |
|---|---|---|---|
| Angle 2-Theta° | d value Angstrom | Intensity Count | Intensity % % |
| 7.090 | 12.4583 | 2858 | 100 |
| 10.907 | 8.1050 | 465 | 16 |
| 12.572 | 7.0351 | 415 | 15 |
| 13.200 | 6.7020 | 561 | 20 |
| 14.321 | 6.1795 | 628 | 22 |
| 14.730 | 6.0088 | 415 | 15 |
| 16.613 | 5.3318 | 540 | 19 |
| 17.129 | 5.1725 | 611 | 21 |
| 17.489 | 5.0668 | 1735 | 61 |
| 18.549 | 4.7795 | 798 | 28 |
| 19.339 | 4.5860 | 769 | 27 |
| 21.532 | 4.1236 | 990 | 35 |
| 22.384 | 3.9685 | 231 | 8 |
| 23.140 | 3.8405 | 389 | 14 |
| 23.655 | 3.7580 | 1486 | 52 |
| 24.914 | 3.5709 | 334 | 12 |
| 25.361 | 3.5090 | 243 | 9 |
| 26.461 | 3.3656 | 277 | 10 |
| 27.472 | 3.2439 | 281 | 10 |
| 28.671 | 3.1110 | 294 | 10 |
| 29.177 | 3.0582 | 430 | 15 |

EXAMPLE 2

Methanol Solvate

Figure 2B:
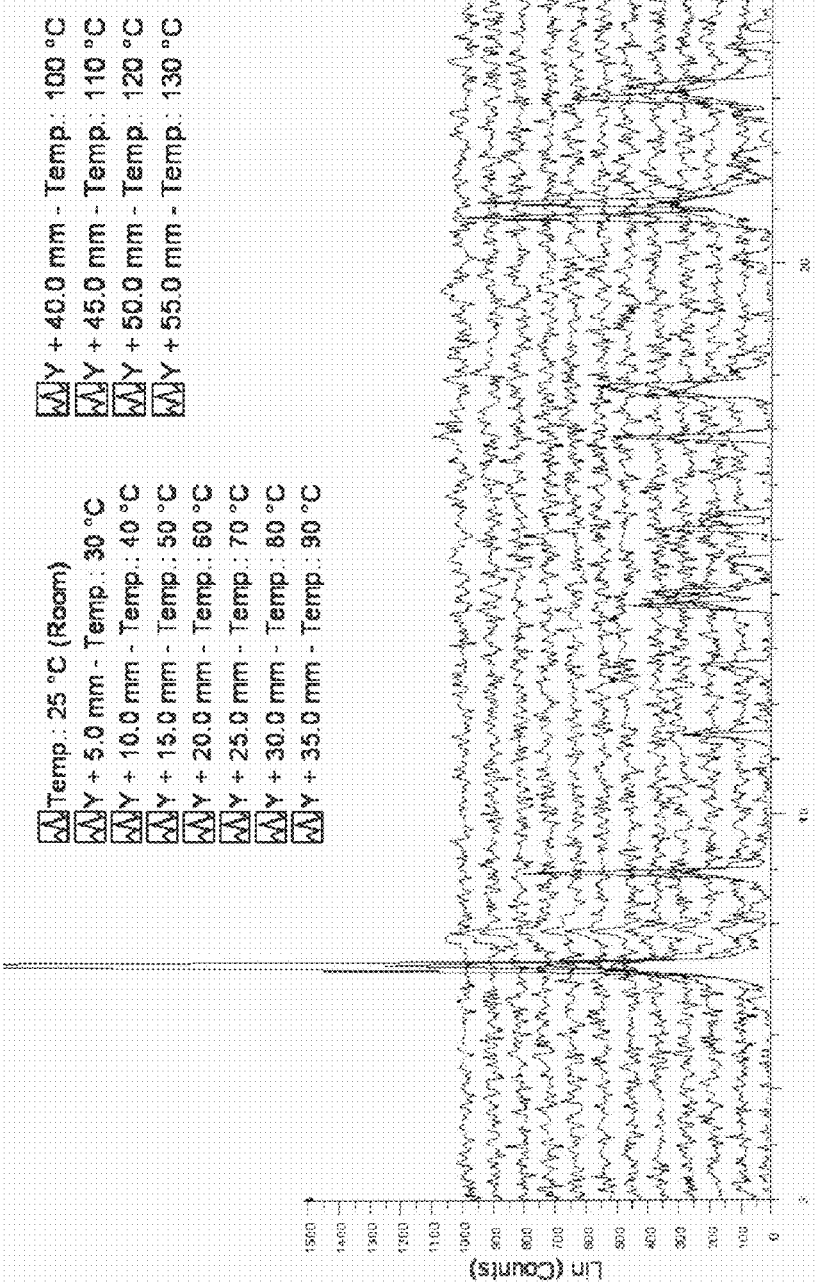
FIG. 2 sets forth identifying data for methanol solvate of the compound of Formula I, above, including 2A, X-ray powder diffraction pattern at 20° C.; and 2B, temperature resolved X-ray powder diffraction patterns, the X-ray powder diffraction patterns being obtained using a diffractometer equipped with a Ni Filter in order to remove most part of the CuKβ radiation.
Figure 4A:
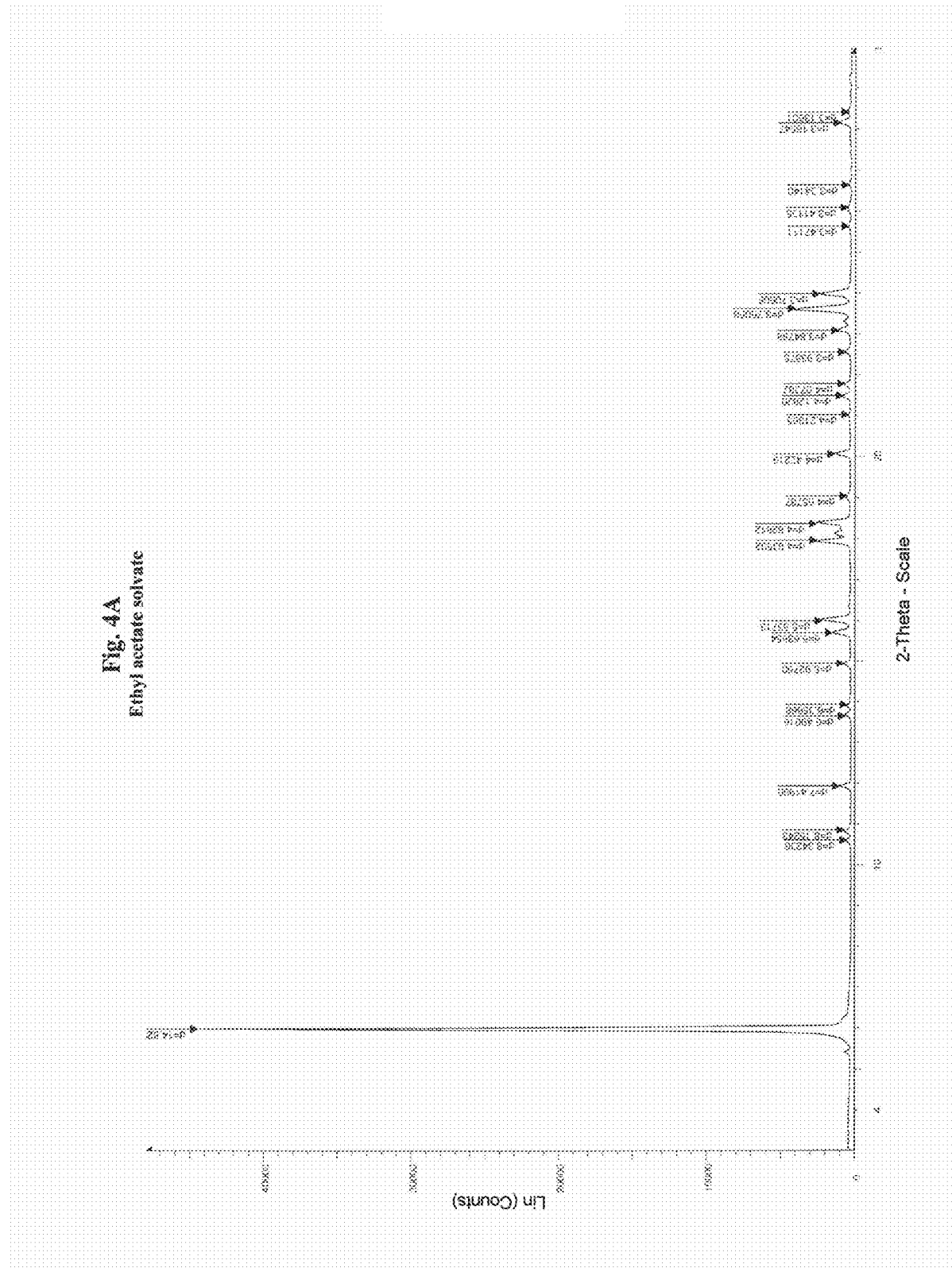
FIG. 4 sets forth identifying data for ethyl acetate solvate of the compound of Formula I, above, including, 4A X-ray powder diffraction pattern at 20° C.; and 4B, temperature resolved X-ray powder diffraction patterns, the X-ray powder diffraction pattern being obtained using a diffractometer equipped with a Ni Filter in order to remove most part of the CuKβ radiation.

In a vial, 0.25 g of the 5,6-dichloro-2-(isopropylamino)-1-(β-L-ribofuranosyl)-1H-benzimidazole (crystallized as form VI) were dissolved in 0.57 g of methanol at room temperature. The solid was completely dissolved into the solvent, and after 15 minutes, a solid recrystallized. The suspension was filtrated gently under vacuum with a glass filter (porosity 3). The X-ray powder diffraction pattern of this powder is presented in FIG. 2A. The behavior of that solvate under heating has been monitored by using TR-XRPD. FIG. 2B shows that after desolvation the solid is poorly crystallized, i.e., close to being amorphous.

TABLE 2

| Characteristic XRPD peaks of maribavir Methanol solvate | | | |
|---|---|---|---|
| Angle 2-Theta° | d value Angstrom | Intensity Count | Intensity % % |
| 7.212 | 12.2474 | 3599 | 100 |
| 8.926 | 9.8990 | 1311 | 36 |
| 11.433 | 7.7332 | 801 | 22 |
| 12.689 | 6.9705 | 747 | 21 |
| 13.782 | 6.4202 | 991 | 28 |
| 14.073 | 6.2879 | 919 | 26 |
| 14.631 | 6.0493 | 663 | 18 |
| 15.216 | 5.8182 | 882 | 25 |
| 15.510 | 5.7084 | 673 | 19 |
| 16.846 | 5.2586 | 986 | 27 |
| 17.740 | 4.9954 | 1044 | 29 |
| 20.121 | 4.4095 | 567 | 16 |
| 20.873 | 4.2523 | 1440 | 40 |
| 21.140 | 4.1991 | 1384 | 39 |
| 21.775 | 4.0782 | 559 | 16 |
| 22.003 | 4.0364 | 544 | 15 |
| 23.039 | 3.8571 | 1050 | 29 |
| 23.217 | 3.8280 | 884 | 25 |
| 23.960 | 3.7109 | 562 | 16 |
| 24.304 | 3.6592 | 511 | 14 |

TABLE 2-continued

Characteristic XRPD peaks of maribavir Methanol solvate

| Angle 2-Theta° | d value Angstrom | Intensity Count | Intensity % % |
|---|---|---|---|
| 25.625 | 3.4735 | 2110 | 59 |
| 26.032 | 3.4201 | 897 | 25 |
| 26.314 | 3.3840 | 627 | 17 |
| 27.289 | 3.2653 | 1510 | 42 |
| 27.600 | 3.2292 | 861 | 24 |
| 27.828 | 3.2033 | 841 | 23 |
| 28.436 | 3.1362 | 584 | 16 |
| 28.752 | 3.1025 | 879 | 24 |

EXAMPLE 3

Acetonitrile Solvate

In a vial, 0.20 g of the 5,6-dichloro-2-(isopropylamino)-1-(β-L-ribofuranosyl)-1H-benzimidazole (crystallized as form VI) were dissolved in 2.77 g of acetonitrile at room temperature. The solid was completely dissolved into the solvent, and after 2 minutes, a solid recrystallized. The suspension was filtrated gently under vacuum with a glass filter (porosity 3). The X-ray powder diffraction pattern of this powder is presented in FIG. 3A.

TABLE 3

Characteristic XRPD peaks of maribavir Acetonitrile solvate

| Angle 2-Theta° | d value Angstrom | Intensity Count | Intensity % % |
|---|---|---|---|
| 7.914 | 11.1617 | 1784 | 70 |
| 9.127 | 9.6809 | 658 | 26 |
| 10.524 | 8.3989 | 1830 | 72 |
| 13.118 | 6.7437 | 1517 | 59 |
| 14.764 | 5.9953 | 534 | 21 |
| 15.359 | 5.7642 | 1287 | 50 |
| 15.872 | 5.5792 | 727 | 28 |
| 17.574 | 5.0424 | 542 | 21 |
| 18.352 | 4.8302 | 1102 | 43 |
| 19.634 | 4.5178 | 642 | 25 |
| 20.076 | 4.4192 | 643 | 25 |
| 20.643 | 4.2992 | 510 | 20 |
| 21.136 | 4.1999 | 1911 | 75 |
| 21.512 | 4.1275 | 597 | 23 |
| 22.158 | 4.0085 | 2561 | 100 |
| 22.759 | 3.9039 | 637 | 25 |
| 24.058 | 3.6960 | 479 | 19 |
| 24.623 | 3.6124 | 349 | 14 |
| 25.323 | 3.5142 | 772 | 30 |
| 26.287 | 3.3875 | 552 | 22 |
| 26.920 | 3.3092 | 437 | 17 |
| 27.360 | 3.2570 | 380 | 15 |
| 27.667 | 3.2215 | 765 | 30 |
| 28.217 | 3.1600 | 413 | 16 |
| 29.736 | 3.0019 | 404 | 16 |

The behavior of that solvate under heating has been monitored by using TR-XRPD. FIG. 3B, which shows that after desolvation the solid could be identified as form V.

EXAMPLE 4

Ethyl Acetate Solvate

In a vial, 0.50 g of the 5,6-dichloro-2-(isopropylamino)-1-(β-L-ribofuranosyl)-1H-benzimidazole (crystallized as form VI) were dissolved in 1.15 g of ethyl acetate at room temperature. The solid was completely dissolved into the solvent, and after 30 minutes, a solid recrystallized. The suspension was filtrated gently under vacuum with a glass filter (porosity 3). The X-ray powder diffraction pattern of this powder is presented FIG. 4A.

TABLE 4

Characteristic XRPD peaks of maribavir Ethylacetate solvate

| Angle 2-Theta° | d value Angstrom | Intensity Count | Intensity % % |
|---|---|---|---|
| 5.955 | 14.8299 | 44556 | 100 |
| 10.596 | 8.3424 | 479 | 1 |
| 10.843 | 8.1524 | 646 | 1 |
| 11.917 | 7.4200 | 962 | 2 |
| 13.632 | 6.4902 | 570 | 1 |
| 13.920 | 6.3567 | 443 | 1 |
| 14.933 | 5.9275 | 690 | 2 |
| 15.703 | 5.6385 | 1465 | 3 |
| 15.993 | 5.5371 | 2174 | 5 |
| 17.956 | 4.9359 | 2507 | 6 |
| 18.360 | 4.8281 | 2541 | 6 |
| 19.038 | 4.6579 | 494 | 1 |
| 20.063 | 4.4222 | 1311 | 3 |
| 21.036 | 4.2197 | 385 | 1 |
| 21.508 | 4.1282 | 752 | 2 |
| 21.798 | 4.0738 | 644 | 1 |
| 22.573 | 3.9358 | 591 | 1 |
| 23.095 | 3.8479 | 1072 | 2 |
| 23.639 | 3.7606 | 3992 | 9 |
| 23.992 | 3.7061 | 2348 | 5 |
| 25.643 | 3.4711 | 366 | 1 |
| 26.100 | 3.4114 | 441 | 1 |
| 26.656 | 3.3414 | 347 | 1 |
| 28.167 | 3.1655 | 946 | 2 |
| 28.437 | 3.1360 | 407 | 1 |

The behavior of that solvate under heating has been monitored by using TR-XRPD. FIG. 4B shows the successive phases: the ethylacetate solvate—form VII and form VI.

EXAMPLE 5

Diethyl Ether Solvate

In a vial, 0.54 g of the 5,6-dichloro-2-(isopropylamino)-1-(β-L-ribofuranosyl)-1H-benzimidazole (crystallized as form VI) were dissolved in 8.0 g of diethyl ether at 20° C. A suspension was obtained. After 16 days of stirring, the major part of the liquid was removed with a pipette. The remaining slurry was analyzed by X-ray powder diffraction (FIG. 5A).

TABLE 5

Characteristic XRPD peaks of maribavir diethylether solvate

| Angle 2-Theta° | d value Angstrom | Intensity Count | Intensity % % |
|---|---|---|---|
| 6.033 | 14.6380 | 3178 | 100 |
| 10.880 | 8.1250 | 1032 | 33 |
| 13.647 | 6.4831 | 728 | 23 |
| 14.139 | 6.2588 | 804 | 25 |
| 15.109 | 5.8590 | 721 | 23 |
| 15.736 | 5.6268 | 623 | 20 |
| 16.442 | 5.3870 | 1217 | 38 |
| 16.844 | 5.2593 | 606 | 19 |
| 18.145 | 4.8850 | 1629 | 51 |
| 18.778 | 4.7216 | 1421 | 45 |
| 19.140 | 4.6331 | 700 | 22 |
| 20.361 | 4.3581 | 608 | 19 |
| 21.164 | 4.1945 | 674 | 21 |
| 21.597 | 4.1112 | 765 | 24 |
| 23.469 | 3.7875 | 542 | 17 |
| 23.741 | 3.7446 | 704 | 22 |

TABLE 5-continued

Characteristic XRPD peaks of maribavir diethylether solvate

| Angle 2-Theta° | d value Angstrom | Intensity Count | Intensity % |
|---|---|---|---|
| 24.113 | 3.6878 | 1515 | 48 |
| 26.000 | 3.4243 | 465 | 15 |
| 28.941 | 3.0826 | 612 | 19 |

The behavior of that solvate under heating has been monitored by using TR-XRPD. FIG. 5B shows the transformation from diethylether solvate to form VII. It is expected that further heating would have led to the solid-solid transformation into form VI.

EXAMPLE 6

N-Butyl Acetate Solvate

In a vial, 1.10 g of the 5,6-dichloro-2-(isopropylamino)-1-(β-L-ribofuranosyl)-1H-benzimidazole (crystallized as form VI) were dissolved in 4.03 g of n-butyl acetate at 20° C. A suspension was obtained. After 1 day of stirring, the major part of the liquid was removed with a pipette. The remaining slurry was analyzed by X-ray powder diffraction (FIG. 6).

TABLE 6

Characteristic XRPD peaks of maribavir n-butyl acetate solvate

| Angle 2-Theta° | d value Angstrom | Intensity Count | Intensity % |
|---|---|---|---|
| 5.900 | 14.9685 | 1331 | 100 |
| 10.840 | 8.1547 | 761 | 57 |
| 11.702 | 7.5558 | 743 | 56 |
| 13.603 | 6.5039 | 695 | 52 |
| 17.911 | 4.9482 | 814 | 61 |
| 18.300 | 4.8440 | 783 | 59 |
| 18.784 | 4.7203 | 780 | 59 |
| 19.703 | 4.5022 | 754 | 57 |
| 20.580 | 4.3122 | 742 | 56 |
| 20.860 | 4.2549 | 753 | 57 |
| 21.661 | 4.0994 | 726 | 55 |
| 21.983 | 4.0400 | 725 | 55 |
| 22.501 | 3.9481 | 792 | 60 |
| 22.996 | 3.8642 | 863 | 65 |
| 23.460 | 3.7889 | 891 | 67 |
| 27.395 | 3.2530 | 715 | 54 |

EXAMPLE 7

1-Propanol Solvate

In a vial, 1.20 g of the 5,6-dichloro-2-(isopropylamino)-1-(β-L-ribofuranosyl)-1H-benzimidazole (crystallized as form VI) were dissolved in 2.25 g of n-butyl acetate at 0° C. A suspension was obtained. After 1 day of stirring, the major part of the liquid was removed with a pipette. The remaining slurry was analyzed by X-ray powder diffraction (FIG. 7).

TABLE 7

Characteristic XRPD peaks of maribavir 1-propanol solvate

| Angle 2-Theta° | d value Angstrom | Intensity Count | Intensity % |
|---|---|---|---|
| 9.154 | 9.6530 | 649 | 31 |
| 9.559 | 9.2443 | 2073 | 100 |
| 10.488 | 8.4282 | 748 | 36 |
| 11.204 | 7.8907 | 1193 | 58 |
| 12.216 | 7.2392 | 619 | 30 |
| 14.025 | 6.3093 | 805 | 39 |
| 14.408 | 6.1423 | 642 | 31 |
| 16.006 | 5.5328 | 644 | 31 |
| 17.796 | 4.9799 | 748 | 36 |
| 18.209 | 4.8678 | 749 | 36 |
| 18.926 | 4.6850 | 1094 | 53 |
| 20.917 | 4.2434 | 1995 | 96 |
| 21.200 | 4.1874 | 680 | 33 |
| 21.436 | 4.1419 | 680 | 33 |
| 22.375 | 3.9702 | 658 | 32 |
| 23.024 | 3.8597 | 1454 | 70 |
| 23.402 | 3.7981 | 576 | 28 |
| 24.031 | 3.7002 | 630 | 30 |
| 25.400 | 3.5037 | 607 | 29 |
| 25.892 | 3.4383 | 607 | 29 |
| 28.533 | 3.1257 | 668 | 32 |
| 28.970 | 3.0796 | 1497 | 72 |

EXAMPLE 8

Hydrochloride Monohydrate

In a round bottom flask, 5.3250 g of the 5,6-dichloro-2-(isopropylamino)-1-(β-L-ribofuranosyl)-1H-benzimidazole (crystallized as form VI) were dissolved in 25 mL of concentrated aqueous hydrochloric acid at room temperature. The solution was completely evaporated under vacuum (T=40° C., P=28 mBar). A crystalline powder was obtained. The X-ray powder diffraction pattern of this powder is presented FIG. 8A.

TABLE 8A

Characteristic XRPD peaks of maribavir hydrochloride monohydrate

| Experimental values | | | Calculated values | | | | | |
|---|---|---|---|---|---|---|---|---|
| Angle 2-Theta° | d value Angstrom | Intensity % | Angle 2-Theta° | d value Angstrom | Intensity % | H | k | l |
| 5.619 | 15.7141 | 23 | 5.612 | 15.7357 | 57 | 1 | 1 | 0 |
| 7.996 | 11.0484 | 100 | 7.939 | 11.1268 | 100 | 2 | 0 | 0 |
| 8.921 | 9.9048 | 15 | 8.878 | 9.9521 | 36 | 2 | 1 | 0 |
| 11.280 | 7.8375 | 4 | 11.237 | 7.8678 | 11 | 2 | 2 | 0 |
| 11.734 | 7.5355 | 3 | 11.724 | 7.5419 | 30 | 1 | 0 | 1 |
| 12.608 | 7.0149 | 2 | 12.568 | 7.0372 | 1 | 3 | 1 | 0 |
| 13.626 | 6.4933 | 1 | 13.603 | 6.5041 | 3 | 2 | 0 | 1 |
| 14.375 | 6.1565 | 5 | 14.339 | 6.172 | 90 | 3 | 2 | 0 |

TABLE 8A-continued

Characteristic XRPD peaks of maribavir hydrochloride monohydrate

| Experimental values | | | Calculated values | | | | | |
|---|---|---|---|---|---|---|---|---|
| Angle 2-Theta ° | d value Angstrom | Intensity % % | Angle 2-Theta ° | d value Angstrom | Intensity % % | H | k | l |
| 15.939 | 5.5559 | 1 | 15.917 | 5.5634 | 1 | 4 | 0 | 0 |
| 16.881 | 5.2479 | 14 | 16.75 | 5.2885 | 35 | 3 | 1 | 1 |
| | | | 16.89 | 5.2452 | 32 | 3 | 3 | 0 |
| 18.162 | 4.8806 | 1 | 18.125 | 4.8904 | 1 | 3 | 2 | 1 |
| 19.857 | 4.4676 | 7 | 19.814 | 4.4771 | 18 | 4 | 1 | 1 |
| 20.997 | 4.2274 | 8 | 20.996 | 4.2278 | 19 | 4 | 2 | 1 |
| 21.506 | 4.1285 | 6 | 21.486 | 4.1324 | 13 | 5 | 2 | 0 |
| 22.232 | 3.9954 | 2 | 22.16 | 4.0081 | 5 | 0 | 0 | 2 |
| 22.613 | 3.9289 | 12 | 22.584 | 3.9339 | 22 | 4 | 4 | 0 |
| 22.842 | 3.8900 | 8 | 22.835 | 3.8912 | 8 | 5 | 0 | 1 |
| | | | 22.835 | 3.8912 | 9 | 4 | 3 | 1 |
| 23.989 | 3.7066 | 3 | 23.915 | 3.7179 | 9 | 2 | 1 | 2 |
| | | | 23.974 | 3.7089 | 1 | 6 | 0 | 0 |
| 24.948 | 3.5662 | 5 | 24.911 | 3.5714 | 18 | 2 | 2 | 2 |
| 25.298 | 3.5176 | 11 | 25.235 | 3.5263 | 30 | 3 | 0 | 2 |
| | | | 25.291 | 3.5186 | 5 | 6 | 2 | 0 |

The single crystal analysis led to the following crystallographic parameter determination:

TABLE 8B

Crystallographic parameters of Maribavir hydrochloride monohydrate

| Crystal system | Tetragonal |
|---|---|
| Space group | P4$_2$2$_1$2 |
| Z | 8 |
| Z' | 1 |
| a (Å) | 22.25 |
| b (Å) | 22.25 |
| c (Å) | 8.016 |
| V (Å$^3$) | 3969.8 |
| Dcalc. (g · cm$^{-3}$) | 1.465 |

Figure 8B:
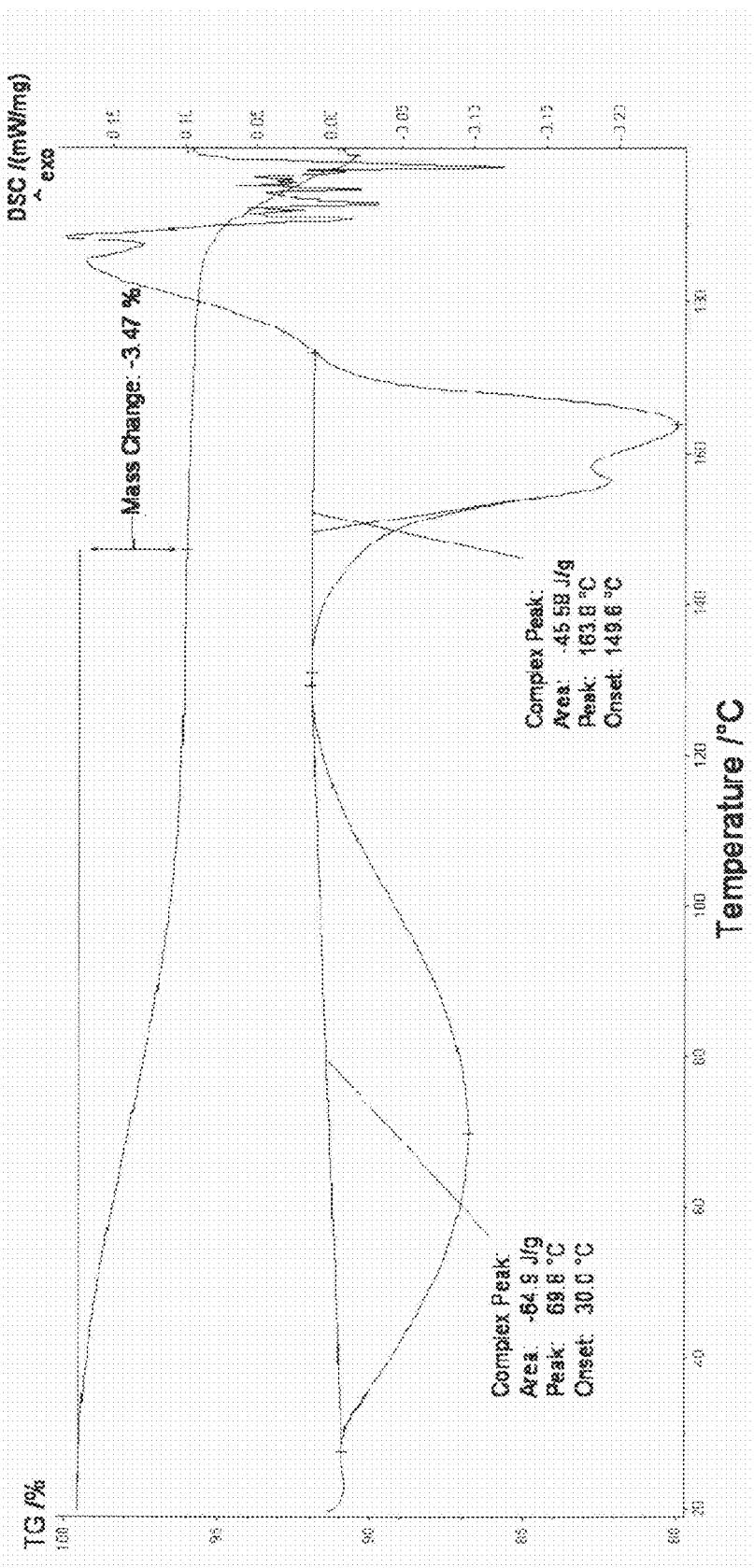
FIG. 8 sets forth identifying data for monohydrate hydrochloride of the compound of Formula I, above, including 8A X-ray powder diffraction pattern at 20° C., the X-ray powder diffraction pattern being obtained using a diffractometer equipped with a Ni Filter in order to remove most part of the CuKβ radiation; and 8B the TGA-DSC curve.

The behavior of that solvate under heating has been monitored by using TGA-DSC. FIG. 8B shows the dehydration of the compound, together with the melting of the newly formed anhydrous form.

EXAMPLE 9

Single crystals were obtained from a slow evaporation of the an ethyl acetate solution of maribavir at 323 K. This temperature above the peritectic transition of the ethylacetate solvate allows the direction crystallization of (the non solvated) Form VI.

A melting point of 469.5 K and a fusion enthalpy of 83.3 J/g were determined from DSC studies.

TABLE 9A

Crystallographic parameters, single crystal X-ray diffraction data collection and resolution data Crystal data

| $C_{15}H_{19}Cl_2N_3O_4$ | Mo Kα radiation |
|---|---|
| Mr = 376.23 | λ = 0.71073 Å |
| Tetragonal | |
| Space group: P4$_1$2$_1$2 | |
| a = 9.2852 (4) Å | μ = 0.386 mm-1 |
| c = 41.602 (2) Å | T = 296 (2) K |
| V = 3586.7 (3) Å$^3$ | Prismatic |
| Z = 8 | Colorless |

TABLE 9A-continued

Crystallographic parameters, single crystal X-ray diffraction data collection and resolution data

| $D_x$ = 1.393 Mg m$^{-3}$ | 0.5 × 0.15 × 0.15 mm |
|---|---|
| $D_m$ not measured | |
| Data collection | |
| CCD area detector diffractometer | 3506 reflections with |
| Phi and ω scans | >2sigma(I) |
| Absorption correction: | $R_{int}$ = 0.0239 |
| Multi-scan sadabs (Sheldrich, Bruker, 2000) | $θ_{max}$ = 26.38° |
| | H = -11 → 11 |
| | K = -11 → 11 |
| 28832 measured reflections | L = -51 → 51 |
| 3678 independent reflections | |
| R[F$^2$ > 2o (F$^2$)] = 0.0404 | $Δ_{pmax}$ = 0.275 e Å$^{-3}$ |
| wR(F2__ = 0.1071 | $Δ_{pmin}$ = -0.183 e Å$^{-3}$ |
| S = 1.084 | Extinction correction: none |
| 3678 reflections | Scattering factors from *International Tables for Crystallography* (Vol. C) |
| H atoms treated by a mixture of independent and constrained refinement | Absolute structure: Flack H D (1983), *Acta Cryst.* A39, 876-881 |
| W = I/o$^2$(F$_o^2$) + (0.0603P)$^2$ + 0.8608P] where P = F$_o^2$ + 2F$_c^2$)/3 | Flack parameter = -0.02 (7) |

TABLE 9B

Intramolecular H-bonds (Å, °)

| D—H...A | D—H | H...A | D...A | D—H...A |
|---|---|---|---|---|
| O3—H3O...O4 | 0.820 | 2.136 | 2.627 | 118.34 |
| N2—H2N...O2 | 0.901 | 2.109 | 2.979 | 161.92 |
| N2—H2N...O1 | 0.901 | 2.383 | 2.934 | 119.53 |

TABLE 9C

Intermolecular H-bonds (Å, °)

| D—H...A | D—H | H...A | D...A | D—H...A |
|---|---|---|---|---|
| O2—H3O...O3 | 0.820 | 2.126 | 2.942 | 173.38 |
| O4—H4O...N1 | 0.801 | 1.937 | 2.736 | 175.06 |

TABLE 9C-continued

| Intermolecular H-bonds (Å, °) | | | | |
|---|---|---|---|---|
| D—H...A | D—H | H...A | D...A | D—H...A |
| O3—H3O...Cl2 | 0.820 | 2.771 | 3.247 | 118.81 |
| O3—H3O...Cl1 | 0.820 | 2.965 | 3.695 | 149.59 |

Anisotropic displacement parameters were refined for non-H atoms. H4O and H2N atoms were located from subsequent Fourier difference syntheses and refined isotropically. All the other H atom positions were calculated.

Figure 9:
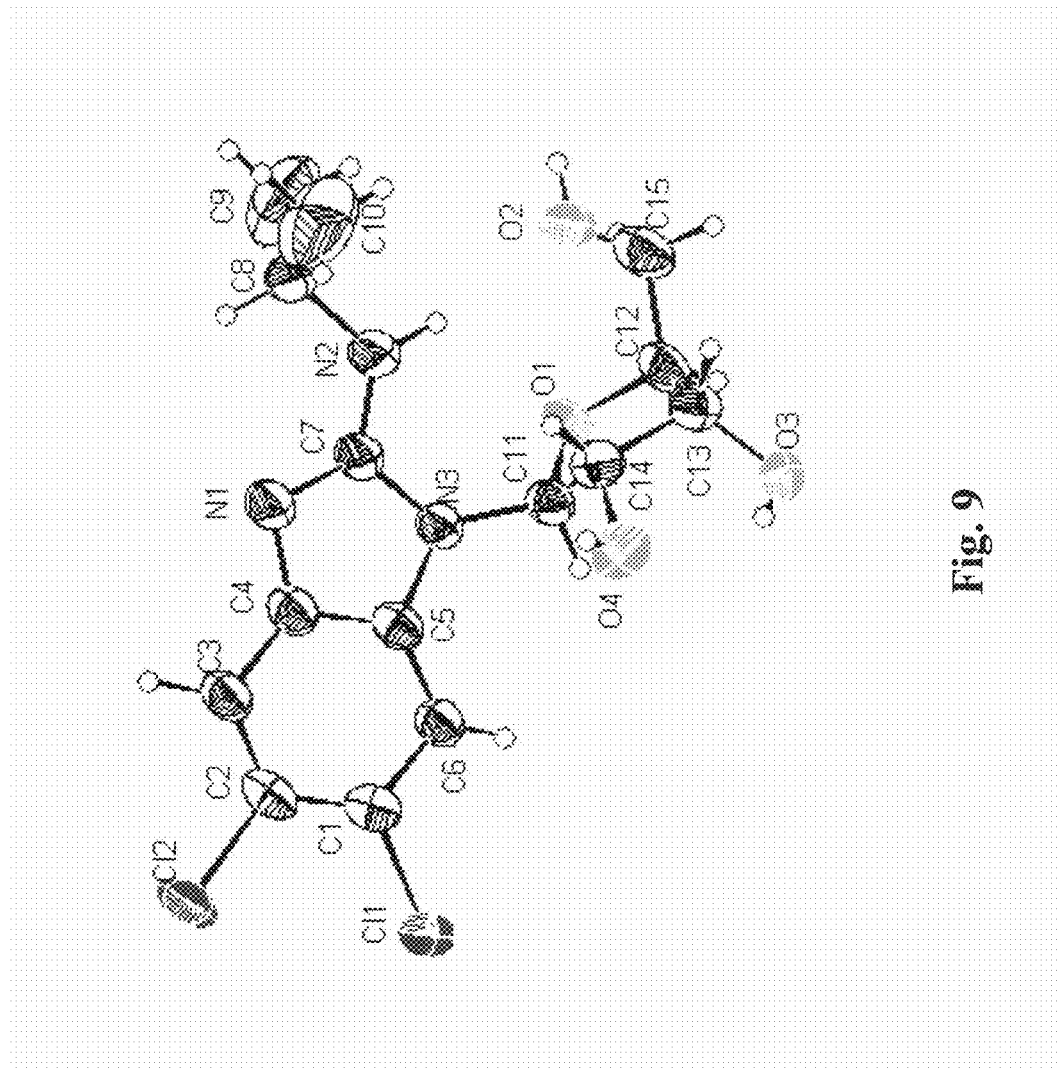
FIG. 9 is an ORTEP drawing of the asymmetric unit of Form VI in the L configuration. All non-H atoms are represented by their displacement ellipsoids drawn at the 50% probability level. H atoms are displayed with an arbitrary radius.

An ORTEP drawing of the asymmetric unit of Form VI was determined (as shown in FIG. 9).

The fractional coordinates of the atoms in form VI are listed in table 9D below:

TABLE 9D

Fractional coordinates of the atoms in Form VI (for Example 9)

| atom Label | Atom type | x/a | y/b | z/c |
|---|---|---|---|---|
| Cl1 | Cl | 1.38082(7) | 0.89331(8) | 0.091947(16) |
| Cl2 | Cl | 1.23358(8) | 1.11972(9) | 0.045202(15) |
| O1 | O | 0.92486(18) | 0.94130(18) | 0.22053(3) |
| N3 | N | 0.9405(2) | 0.9974(2) | 0.16604(4) |
| O4 | O | 0.8751(2) | 0.6661(2) | 0.16268(4) |
| N1 | N | 0.8384(2) | 1.1596(2) | 0.13264(5) |
| C5 | C | 1.0305(2) | 1.0074(2) | 0.13922(5) |
| O3 | O | 0.9270(2) | 0.5895(2) | 0.22234(4) |
| H3O | H | 0.9706 | 0.5805 | 0.2053 |
| C6 | C | 1.1575(2) | 0.9403(3) | 0.13157(5) |
| H6 | H | 1.1994 | 0.8727 | 0.1452 |
| C7 | C | 0.8261(2) | 1.0910(3) | 0.16033(5) |
| C11 | C | 0.9465(2) | 0.8826(2) | 0.18960(4) |
| H11 | H | 1.0418 | 0.8373 | 0.1888 |
| C14 | C | 0.8324(2) | 0.7676(3) | 0.18575(5) |
| H14 | H | 0.7399 | 0.8109 | 0.1798 |
| C13 | C | 0.8250(3) | 0.7035(3) | 0.21955(6) |
| H13 | H | 0.7275 | 0.6694 | 0.2244 |
| C1 | C | 1.2208(2) | 0.9784(3) | 0.10236(5) |
| C12 | C | 0.8663(3) | 0.8297(3) | 0.24125(5) |
| H12 | H | 0.9416 | 0.7980 | 0.2562 |
| N2 | N | 0.7199(3) | 1.1065(3) | 0.18153(5) |
| C3 | C | 1.0294(3) | 1.1449(3) | 0.09021(5) |
| H3 | H | 0.9875 | 1.2121 | 0.0765 |
| C8 | C | 0.5993(3) | 1.2057(3) | 0.17685(6) |
| H8 | H | 0.6158 | 1.2633 | 0.1575 |
| C4 | C | 0.9651(2) | 1.1087(3) | 0.11920(5) |
| C2 | C | 1.1576(2) | 1.0781(3) | 0.08223(5) |
| C9 | C | 0.5898(6) | 1.3039(5) | 0.20568(11) |
| H9A | H | 0.5748 | 1.2474 | 0.2247 |
| H9B | H | 0.5108 | 1.3694 | 0.2030 |
| H9C | H | 0.6778 | 1.3574 | 0.2077 |
| C10 | C | 0.4649(5) | 1.1212(6) | 0.17310(14) |
| H10A | H | 0.4749 | 1.0561 | 0.1553 |
| H10B | H | 0.3858 | 1.1853 | 0.1692 |
| H10C | H | 0.4471 | 1.0673 | 0.1924 |
| C15 | C | 0.7453(3) | 0.8940(3) | 0.26021(5) |
| H15A | H | 0.7098 | 0.8249 | 0.2758 |
| H15B | H | 0.7786 | 0.9787 | 0.2717 |
| O2 | O | 0.6337(2) | 0.9323(2) | 0.23849(4) |
| H2O | H | 0.5665 | 0.9680 | 0.2485. |
| H2N | H | 0.714(3) | 1.056(3) | 0.2000(7) |
| H4O | H | 0.814(4) | 0.669(4) | 0.1492(10). |

Data collection: Bruker SMART. Cell refinement: Bruker SMART. Data reduction: Bruker SAINT. Program(s) used to solve structure: SHELXS-97 (Sheldrick, 1990). Program(s) used to refine structure: SHELXL97 (Sheldrick, 1997). Molecular graphics: diamond (Brandenburg and Berndt, 1999). Software used to prepare material for publication: SHELXS-97 and PLATON (Speck, 2003).

A number of patent and non-patent documents are cited in the foregoing specification in order to describe the state of the art to which this invention pertains. The entire disclosure of each of these citations is incorporated by reference herein.

While various embodiments of the present invention have been described and/or exemplified above, numerous other embodiments will be apparent to those skilled in the art upon review of the foregoing disclosure. The present invention is, therefore, not limited to the particular embodiments described and/or exemplified, but is capable of considerable variations and modifications without departure from the scope of the appended claims. Furthermore, the transitional phrases "comprising", "consisting essentially of" and "consisting of" define the scope of the appended claims, in original and amended form, with respect to what unrecited additional claim elements or steps. The term "comprising" is intended to be inclusive or open-ended and does not exclude additional, unrecited elements, methods step or materials. The phrase "consisting of" excludes any element, step or material other than those specified in the claim, and, in the latter instance, impurities ordinarily associated with the specified materials. The phrase "consisting essentially of" limits the scope of a claim to the specified elements, steps or materials and those that do not materially affect the basic and novel characteristic(s) of the claimed invention. All compositions or formulations identified herein can, in alternate embodiments, be more specifically defined by any of the transitional phases "comprising", "consisting essentially of" and "consisting of".

REFERENCES

1. Brandenburg, K. (2001), Diamond version 2.1, Crystal Impact, Gbr;
2. Bruker (2001). SMART. Version 5.622. Bruker AXS Inc., Madison, Wis., USA
3. Bruker (1999). SAINT. Version 5.6.0 Bruker AXS Inc., Madison, Wis., USA
4. Flack, H. D. (1986), Acta Cryst., A39, 876-881
5. Sheldrick, G. M. (1997). SHELXTL. Version 6.10 Bruker AXS Inc., Madison, Wis., USA
6. Sheldrick, G. M. (2001). SADABS, University of Gottingen, Germany;
7. U.S. Pat. No. 6,077,832 to Chamberlain et al.
8. U.S. Pat. No. 6,469,160 to Glover et al.
9. U.S. Pat. No. 6,482,939 to Hodson and Huang The invention relates to the novel unsolvated crystalline forms and solvates described herein, both in pure form and in admixture with other such polymorphs and/or known forms or solvates of the compound of formula (I), above. For example, the admixture may include the combinations listed in Table 10 below.

TABLE 10

List of crystalline phase admixtures of maribavir:

| Component 1 | Component 2 | Component 3 (Optional) |
|---|---|---|
| Form VI | Form VII | One or more other solid phases of maribavir. |
| Form VI | methanol solvate | One or more other solid phases of maribavir. |
| Form VI | acetonitrile solvate | One or more other solid phases of maribavir. |
| Form VI | ethyl acetate solvate | One or more other solid phases of maribavir. |
| From VI | diethyl ether solvate | One or more other solid phases of maribavir. |

TABLE 10-continued

List of crystalline phase admixtures of maribavir:

| Component 1 | Component 2 | Component 3 (Optional) |
|---|---|---|
| Form VI | n-butyl acetate solvate | One or more other solid phases of maribavir. |
| Form VI | 1-propanol solvate | One or more other solid phases of maribavir. |
| Form VI | monohydrate hydrochloride | One or more other solid phases of maribavir. |

What is claimed is:

1. Crystalline Form VII of 5,6-dichloro-2-(isopropylamino)-1-β-L-ribofuranosyl)-1H-benzimidazole having an X-ray powder diffraction pattern selected from the group consisting of those substantially as shown in FIG. 1A.

2. A crystalline form of 5,6-dichloro-2-(isopropylamino)-1-β-L-ribofuranosyl)-1H-benzimidazole having an X-ray powder diffraction pattern selected from the group consisting of those substantially as shown in FIGS. 2A-8A.

3. A pharmaceutical composition comprising a crystalline form of 5,6-dichloro-2-(isopropylamino)-1-β-L-ribofuranosyl)-1H-benzimidazole according to claim 1 and at least one pharmaceutically acceptable carrier.

4. A pharmaceutical composition according to claim 3 in the form of a powder, tablet, capsule or suspension.

5. A composition comprising an admixture of crystalline Form VII of 5,6-dichloro-2-(isopropylamino)-1-β-L-ribofuranosyl)-1H-benzimidazole, together with at least one of Form I, Form II, ethanol solvate, Form IV, Form V, Form VI and amorphous 5,6-dichloro-2-(isopropylamino)-1-β-L-ribofuranosyl)-1H-benzimidazole.

6. A composition comprising an admixture of a crystalline form of 5,6-dichloro-2-(isopropylamino)-1-β-L-ribofuranosyl)-1H-benzimidazole according to claim 2, together with at least one of Form I, Form II, ethanol solvate, Form IV, Form V, Form VI and amorphous 5,6-dichloro-2-(isopropylamino)-1-β-L-ribofuranosyl)-1H-benzimidazole.

7. A method for treatment or prophylaxis of a herpes viral infection in a patient in need thereof comprising administering to said patient an effective anti-viral amount of crystalline Form VII of 5,6-dichloro-2-(isopropylamino)-1-β-L-ribofuranosyl)-1H-benzimidazole.

8. A method according to claim 7, wherein said herpes viral infection is cytomegalovirus (CMV).

9. A method for treatment or prophylaxis of a herpes viral infection in a patient in need thereof comprising administering to said patient an effective anti-viral amount of a crystalline form of 5,6-dichloro-2-(isopropylamino)-1-β-L-ribofuranosyl)-1H-benzimidazole, according to claim 2.

10. A method according to claim 7, wherein said herpes viral infection is cytomegalovirus (CMV).

* * * * *